US009239329B2

(12) United States Patent
Suda et al.

(10) Patent No.: US 9,239,329 B2
(45) Date of Patent: Jan. 19, 2016

(54) METHOD OF MEASURING INTERACTION BETWEEN BIOMATERIAL AND SUGAR CHAIN, METHOD OF EVALUATING BIOMATERIAL IN SUGAR CHAIN SELECTIVITY, METHOD OF SCREENING BIOMATERIAL, METHOD OF PATTERNING BIOMATERIALS, AND KITS FOR PERFORMING THESE METHODS

(75) Inventors: Yasuo Suda, Kagoshima (JP); Tomoaki Nishimura, Hyogo (JP); Yuko Kishimoto, Hyogo (JP); Sakiko Yamashita, Kagoshima (JP); Sachiko Tsuruta, Hyogo (JP); Masahiro Wakao, Kagoshima (JP); Toshiomi Okuno, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 971 days.

(21) Appl. No.: 11/818,695

(22) Filed: Jun. 15, 2007

(65) Prior Publication Data

US 2008/0145838 A1    Jun. 19, 2008

(30) Foreign Application Priority Data

Dec. 18, 2006  (JP) .................................. 2006-340554

(51) Int. Cl.

| G01N 33/53  | (2006.01) |
|---|---|
| G01N 33/68  | (2006.01) |
| G01N 33/569 | (2006.01) |
| G01N 33/543 | (2006.01) |
| G01N 33/92  | (2006.01) |

(52) U.S. Cl.
CPC .......... *G01N 33/569* (2013.01); *G01N 33/5308* (2013.01); *G01N 33/5432* (2013.01); *G01N 33/68* (2013.01); *G01N 33/92* (2013.01); *G01N 2400/00* (2013.01)

(58) Field of Classification Search
None
See application file for complete search history.

(56) References Cited

U.S. PATENT DOCUMENTS

| 5,478,741 | A  | * | 12/1995 | Maret et al. ................... 435/342 |
|---|---|---|---|---|
| 5,714,166 | A  |   | 2/1998  | Tomalia et al. |
| 5,886,143 | A  |   | 3/1999  | Theodore et al. |
| 6,756,354 | B2 |   | 6/2004  | Nelson |
| 7,183,067 | B2 | * | 2/2007  | Suda et al. ...................... 435/7.5 |
| 7,320,867 | B2 | * | 1/2008  | Suda et al. ...................... 435/7.1 |
| 2004/0166508 | A1 |  | 8/2004 | Pawlak et al. |
| 2005/0059014 | A1 |  | 3/2005 | Pawlak et al. |
| 2005/0079528 | A1 |  | 4/2005 | Takiguchi et al. |
| 2005/0130240 | A1 |  | 6/2005 | Lin et al. |
| 2005/0287552 | A1 |  | 12/2005 | Lin et al. |
| 2007/0213523 | A1 |  | 9/2007 | Suda et al. |
| 2009/0240032 | A1 |  | 9/2009 | Suda et al. |

FOREIGN PATENT DOCUMENTS

| EP | 0869126 B1       | 7/2002  |
|---|---|---|
| EP | 1726596          | 11/2006 |
| JP | 7-252288 A       | 10/1995 |
| JP | 2002-80488 A     | 3/2002  |
| JP | 2002-228661      | 8/2002  |
| JP | 2002228661       | 8/2002  |
| JP | 2003-83969 A     | 3/2003  |
| JP | 2005084028       | 3/2005  |
| JP | 2005537486       | 12/2005 |
| JP | 2005537487       | 12/2005 |
| JP | 2006-78418 A     | 3/2006  |
| JP | 2006-1538 A      | 6/2006  |
| JP | 2006-156831 A    | 6/2006  |
| WO | 96/17613 A1      | 6/1996  |
| WO | 01/86301 A1      | 11/2001 |
| WO | WO-0232404       | 4/2002  |
| WO | WO-2004108165    | 12/2004 |
| WO | WO-2005/075453 A1 | 8/2005 |
| WO | WO-2005077965    | 8/2005  |
| WO | 2006/126689 A1   | 11/2006 |

OTHER PUBLICATIONS

Arano et al. Preparation of a novel clustered oligosaccharide-ligand containing multi-units of heparin partial structure and its application for chip technology. Chemical society of Japan, the 82th Fall Meeting, Sep. 10, 2002, p. 137.*
Suda et al. Immobilization and clustering of structurally defined oligosaccharides for sugar chips: an improved method for surface plasmon resonance analysis of protein-carbohydrate interactions. Bioconjugate Chem. 2006, vol. 17, pp. 1125-1135.*
Hayashi et al. Synthesis, designed assembly and biotinylation of sulfated oligosaccharide and its application to surface plasmon resonance. Tentative Lecture Proceedings. Chemical Society of Japan 2001, vol. 79, No. 2, p. 1042.*
Stevens et al. Glycan microarray technologies: tools to survey host specificity of influenza viruses. Nature 2006, vol. 4, pp. 857-864.*

(Continued)

*Primary Examiner* — Shafiqul Haq
(74) *Attorney, Agent, or Firm* — Morrison & Foerster LLP

(57) ABSTRACT

This invention provides a method of screening or patterning a biomaterial in terms of their specificities to sugar chains by performing real-time and comprehensive measurement of an interaction between sugar chains and the biomaterial concurrently with a very small amount of the biomaterial without labeling. It is a method of measuring an interaction between a biomaterial and a sugar chain(s), the method including: bringing a solution containing the biomaterial in contact with a ligand carrier, the ligand carrier including a support whose surface includes a metal, and a ligand conjugate(s) immobilized independently on the surface, the ligand carrier carrying the ligand conjugate(s) in such a manner that 1 to 500 kinds of the ligand conjugate(s) is immobilized per $cm^2$, and each ligand conjugate having a structure in which a sugar chain is bonded with a linker compound having a sulfur atom, and the biomaterial being at least one selected from the groups of proteins, viruses, cells, microorganisms, liposome, and micelles.

7 Claims, 6 Drawing Sheets

(56) References Cited

OTHER PUBLICATIONS

Stevens et al. Glycan microarray analysis of the hemagglutinins from modern and pandemic influenza viruses reveals different receptor specificities. J. Mol. Biol. 2006, vol. 355, pp. 1143-1155.*

Nobusawa et al. Change in receptor-binding specificity of recent human influenza A viruses (H3N2): a single amino acid change in hemagglutinin altered its recognition of sialyloligosaccharides. Virology 2000, vol. 278, pp. 587-596.*

Banfield, B. et al. (1995). "Evidence for an Interaction of Herpes Simplex Virus with Chondroitin Sulfate Proteoglycans during Infection," *Virology* 208:531-539.

Bergefall, K. et al. (Sep. 2005). "Chondroitin Sulfate Characterized by the E-disaccharide Unit Is a Potent Inhibitor of Herpes Simplex Virus Infectivity and Provides the Virus Binding Sites on gro2C Cells," *The Journal of Biological Chemistry* 280(37):32193-32199.

Misinzo, G. et al. (Apr. 2006). "Porcine Circovirus 2 Uses Heparan Sulfate and Chondroitin Sulfate B Glycosaminoglycans as Receptors for Its Attachment to Host Cells," *Journal of Virology* 80(7):3487-3494.

Shukla, D. et al. (Aug. 2001). "Herpesviruses and heparan sulfate: an intimate relationship in aid of viral entry," *The Journal of Clinical Investigation* 108(4):503-510.

Uyama, T. et al. (Dec. 2006). "Chondroitin 4-*O*-Sulfotransferase-1 Regulates E Disaccharide Expression of Chondroitin Sulfate Required for Herpes Simplex Virus Infectivity," *The Journal of Biological Chemistry* 281(50):38668-38674.

"Development and Evaluation of Bio Diagnostic Agents, and Companies thereof." (Aug. 31, 1990) CMC technical library 146, CMC publishing Co., Ltd., pp. 92-97 and pp. 109-113.

Suzuki et al. (1992). "Structural Determination of Gangliosides that Bind to Influenza A, B, and C Viruses by an Improved Binding Assay: Strain-Specific Receptor Epitopes in Sialo-Sugar Chains," Virology 189:121-131.

Herold et al. (Jun. 1996). "Differences in the Susceptibility of Herpes Simplex Virus Types 1 and 2 to Modified Heparin Compounds Suggest Serotype Differences in Viral Entry," Journal of Virology, 70(6):3461-3469.

Ito et al. (1997). "Receptor Specificity of Influenza A Viruses Correlates with the Agglutination of Erythrocytes from Different Animal Species," Virology 227:493-499.

Trybala et al. (Oct. 2000). "Herpes Simplex Virus Types 1 and 2 Differ in Their Interaction with Heparan Sulfate," Journal of Virology, 74(19):9106-9114.

Otsuka et al. (2001). "Quantitative and Reversible Lectin-Induced Association of Gold Nanoparticles Modified with I-Lactosyl-a-mercapto-poly(ethylene glycol)," American Journal of Chemical Society, 123:8226-8230.

Fuente et al. (2001). "Gold Glyconanoparticles as Water-Soluble Polyvalent Models to Study Carbohydrate Interactions," Angew. Chem. Int. Ed., 40(12)2258-2261.

Feizi et al. (2003). "Carbohydrate microarrays—a new set of technologies at the frontiers of glycomics," Current Opinion in Structural Biology, 13:637-645.

Manimala et al. (2006). "High-Throughput Carbohydrate Microarray Analysis of 24 Lectins," Angew. Chem. Int. Ed. 45:3607-3610.

CMC Technical Library 146. (Aug. 31, 1990). *Development and Evaluation of Bio Diagnostic Agents, and Companies Thereof.* First Edition, CMC Publishing Co., Ltd., pp. 92-97, 108-113 (partial English translation attached, 4 pages).

De La Fuente, J. M. et al. (2001). "Gold Glyconanoparticles as Water-Soluble Polyvalent Models to Study Carbohydrate Interactions," *Angewandte Chemie International Edition* 40(12):2257-2261.

Canadian Office Action mailed Mar. 11, 2010, for CA application No. 2591496 filed Jun. 15, 2007, 4 pages.

Gambaryan et al. (1997). "Specification of Receptor-Binding Phenotypes of Influenza Virus Isolates From Different Hosts Using Synthetic Sialylglycopolymers: Non-Egg-Adapted Human H1 and H3 Influenza A and Influenza B Viruses Share a Common High Binding Affinity for 6'- sialyl(N-acetyllactosamine)," *Virology* 232:345-350.

Office Action received for Japanese Patent Application No. 2007-324036, mailed on Dec. 20, 2011, 6 pages (4 pages of English Translation and 2 pages of Japanese Office Action).

Office Action received for Japanese Patent Application No. 2007-324036, mailed on Sep. 27, 2011, 4 pages (3 pages of English translation and 1 page of Office Action).

Suda, Yasuo, "Development of Detection and Diagnosis Technique using Sugar Chip", Heisei 17-nen, General Research Report, Apr. 2006, 16 pages (Partial English Translation only).

Wakao et al., "Chemical and Enzymatic Synthesis of Sialyliacto Type Oligosaccharide and its Application to Sugar Chip", Proceedings of Chemical Society of Japan, vol. 86, No. 2, Mar. 13, 2006, 5 pages (Partial English Translation only).

Non Final Office Action received for U.S. Appl. No. 10/526,775, mailed on Feb. 9, 2007, 13 pages.

Notice of Allowance received for U.S. Appl. No. 10/526,775, mailed on Jul. 26, 2007, 8 pages.

Non Final Office Action received for U.S. Appl. No. 10/526,938, mailed on Dec. 29, 2005, 12 pages.

Notice of Allowance received for U.S. Appl. No. 10/526,938, mailed on Aug. 28, 2006, 11 pages.

Office Action received for Korean Patent Application No. 10-2005-7003969, mailed on May 29, 2006, 5 pages (3 pages of English Translation and 2 pages).

Office Action received for Korean Patent Application No. 10-2005-7004021, mailed on May 26, 2006, 7 pages (4 pages of English Translation and 3 pages).

Wells et al., "Solid-Phase Dendrimer Synthesis", Biopolymers, vol. 47, 1998, pp. 381-396.

Arano et al., "Preparation of a Novel Clustered Oligosaccharide-Ligand Containing Multi-units of heparin partial structure and its application for chip Technology", The chemical Society of Japan 82th Fall meeting, Sep. 10, 2002, p. 137(1C1-11).

Arano et al., "Synthesis of a Conjugate Having Heparin Partial Structure and a Distal Disulfide Group and its Application to Chip Technology", Tentative Lecture Proceedings II in the 79th Spring Meeting, Chemical Society of Japan, Mar. 15, 2001, p. 1042(4G305).

Fazio et al., "Synthesis of Sugar Arrays in Microtiter Plate", J. Am. Chem. Soc., vol. 124, No. 48, 2002, pp. 14397-14402.

Feizi et al., "Oligosaccharide Microarrays to Decipher the Glyco Code", Nature Reviews, vol. 5, Jul. 2004, pp. 582-588.

Fukase et al., "Functional Fluorescence Labeling of Carbohydrates and its Use for Preparation of Neoglycoconjugates", Journal of Carbohydrate Chemistry, vol. 13, No. 5, 1994, pp. 715-736.

Hayashi et al., "Assembly of Saccharide by Multi-Functional Linker and Application to Surface Plasmon Resonance Analysis and Affinity Chromatography", Tentative Lecture Proceedings, Chemical Society of Japan, vol. 83, No. 2, 313/2003, p. 952 (2G2-48).

Hayashi et al., "Ryusanka Oligo-to no Shugoka, Biotin-ka oyobi Sono Hyomen Plasmon Kyomei eno Oyo", The Chemical Society of Japan Dai 79 Shunki Nenkai, Mar. 2001, p. 1042 (4G304).

Hayashi et al., "Ryusanka Oligo-to no Shugoka, Biotin-ka to Sono Sensor chip eno Oyo", Dai 23 Kai The Japanese Society of Carbohydrate Research Nenkai Yoshishu, Jul. 2002, p. 75 (PI-05).

Hayashi et al., "Synthesis of a Novel Linker Molecule for Assembly and Immobilization of Reducing Saccharides", Chemical Society of Japan, vol. 82, Sep. 10, 2002, p. 137 (1C1-12).

Horan et al., "Nonstatistical Binding of a Protein to Clustered Carbohydrates", PNAS, vol. 96, No. 21, Oct. 12, 1999, pp. 11782-11786.

Houseman et al., "Carbohydrate Arrays for the Evaluation of Protein Binding and Enzymatic Modification", Chemistry & Biology, vol. 9, Apr. 2002, pp. 443-454.

Kato et al., "Using Model Substrates to Study the Dependence of Focal Adhesion Formation on the Affinity of Integrin-Ligand Complexes", Biochemistry, vol. 43, No. 10, 2004, pp. 2699-2707.

Koshida et al., "An Efficient Method for the Assembly of Sulfated Oligosaccharides Using Reductive Amination", Tetrahedron Letters, vol. 42, 2001, pp. 1293-1296.

Koshida et al., "Synthesis and Biological Activity of Oligomer-Model Ccompounds Containing Units of a key Platelet-Binding Binding Disaccharide of Heparin", Tetrahedron Letters, vol. 40, 1999, pp. 5725-5728.

(56) References Cited

OTHER PUBLICATIONS

Koshida et al., "Synthesis of Oligomeric Assemblies of a Platelet-Binding key Disaccharide in Heparin and their Biological Activities", Tetrahedron Letters, vol. 42, 2001, pp. 1289-1292.
Woller et al., "The Lectin-Binding Properties of Six Generations of Mannose-Functionalized Dendrimers", Organic Letters, vol. 4, No. 1, 2002, pp. 7-10.
Worner et al., "Polynitrile-and Polyamine-Functional Poly(Trimethylene Imine)Dendrimers", Angew. Chem. Int. Ed. Engl., vol. 32, No. 9, 1993, pp. 1306-1311.
Lindhorst et al., "Glycocoating of Oligovalent Amines: Synthesis of Thiourea-Bridged Cluster Glycosides from Glycosyl Isothiocyanates", Angew. Chem. Int. Ed. Engl., vol. 35, No. 17, 1996, pp. 1953-1956.
Mach et al., "Nature of the Interaction of Heparin with Acidic Fibroblast Growth Factor", Biochemistry, vol. 32, No. 20, 1993, pp. 5480-5489.
Matsuura et al., "A Quantitative Estimation of Carbohydrate-Carbohydrate Interaction Using Clustered Oligosaccharides of Glycolipid Monolayers and of Artificial Glycoconjugate Polymers by Surface Plasmon Resonance", J. Am. Chem. Soc, vol. 122, No. 30, 2000, pp. 7406-7407.
Park et al., "Carbohydrate Chips for Studying High-Throughput Carbohydrate-Protein Interactions", J. Am. Chem. Soc., vol. 126, No. 15, 2004, pp. 4812-4819.
Ratner et al., "Probing Protein-Carbohydrate Interactions with Microarrays of Synthetic Oligosaccharides", ChemBioChem, vol. 5, 2004, pp. 379-382.
Sumida et al., "Ryusanka Oligo-to o Koteika shita Sugar Chip no Kaihatsu to Hyomen Plasmon Kyomeiho eno Oyo", Seikagaku, vol. 74, No. 8, Aug. 25, 2002, p. 849 (3P-047).
Suda, Yasuo, "Ryusanka Tennen Tato no Kino Domain Kozo no Saikochiku to Sensor Chip eno Oyo",The Chemical Society of Japan Dai 81 Shunki Nenkai Nen Koen Yokoshu II., Mar. 2002, p. 949 (1F6-33).
Tomalia et al., "A New Class of Polymers: Starburst-Dendritic Macromolecules", Polymer Journal, vol. 17, No. 1, 1985, pp. 117-132.
Office Action received for Japanese Patent Application No. 2012-260396, mailed on Mar. 11, 2014, 5 pages (3 pages of English Translation and 2 pages).
Hayashi et al., "Assembly of Saccharide by Multi-Functional Linker and Application to Surface Plasmon Resonance Analysis and Affinity Chromatography", Tentative Lecture Proceedings, Chemical Society of Japan, vol. 83, No. 2, Mar. 3, 2003, p. 952 (2G2-48).
Akio Arano et al., "Disulfide Ketsugo O Yusuru Linker O Ketsugo saseta Heparin Bubun Kozo no Gosei to Chip Technology eno Oyo", CSJ: The Chemical Society of Japan Dai 79 Shunki Nenkai (2001) Koen Yokoshu II, Mar. 2001, p. 1042 (4G305).
Hayashi Kusumoto et al., "Tosa no Shugoka to Koteika no Tame no Shinki Linker Bunshi no Gosei", CSJ: The Chemical Society of Japan Koen Yokoshu, Sep. 10, 2002, vol. 82, p. 137 (1C1-12).
Hayashi Kusumoto et al., "Taki Yotogata Linker o Mochiita Tosa no Shugoka to Hyomen Plasmon Kyomeiho Kalseki Narabi ni Affinity Chromatography eno Oyo", CSJ: The Chemical Society of Japan Yokoshu, Mar. 3, 2003, vol. 83, No. 2, p. 952 (2G2-48).
Office Action Received for Japanese Patent Application No. 2012-260396, mailed on Nov. 18, 2014, 13 pages (9 pages of English Translation and 4 pages).
Sakiko et al., "Chemoenzymatic Synthesis of Sialyllacto Type Oligosaccharide and Its Application to Sugar Chip", The Summary of the 26th Annual Meeting of the Japanese Society of Carbohydrate Research, Jul. 28, 2006, p. 148, p. 2-31. (English Abstract Attached).
Suda, Yasuo, "Sugar Chips: Advanced Analytical Systems for the Binding Interaction of Sugar Chains with Proteins, Cells or Viruses", 2006 International Conference on Chemical and Molecular Technologies, Tainan, Taiwan, Dec. 7-9, 2006, Dec. 7, 2006, pp. 30-31.
Japan Science and Technology Agency (JST), "Establishment of a Venture Business for Providing a New Bio Device "Sugar Chip"", Japan Science and Technology Agency Report No. 350, Oct. 3, 2006, 7 pages (4 pages of English Translation and 3 pages).

\* cited by examiner

FIG. 2
| SGNP | — | Galβ1-4Glc | NeuSAcα2-6 Galβ1-4Glc NAcβ1-6Glc | NeuSAcα2-6 Galβ1-4Glc Nacβ1-6Glc |
|---|---|---|---|---|
| Virus | + | + | — | + |
| Side | 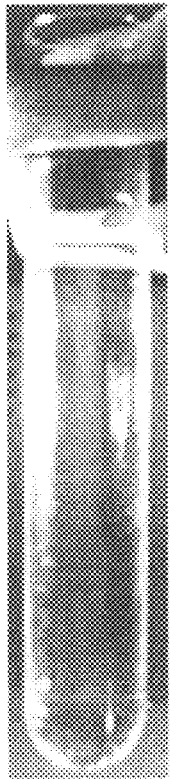 | 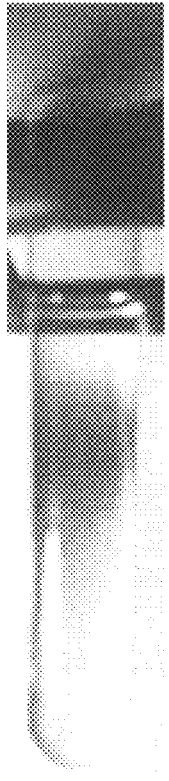 | 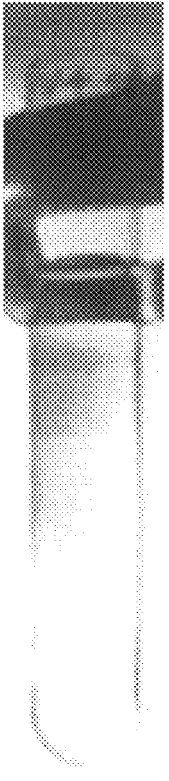 | 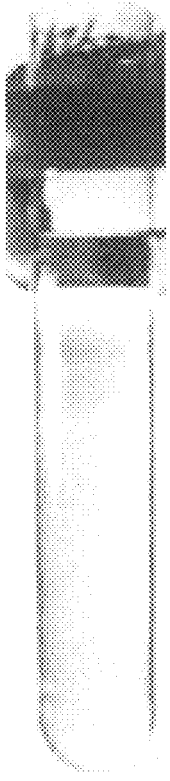 |
| Bottom | — | 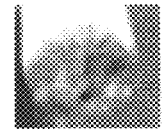 | 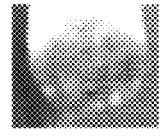 | 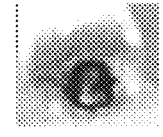 |

FIG. 3

| LECTIN | 1 | 2 | 3 | 4 | 5 | 6 | 7 | 8 | 9 | 10 | 11 | 12 |
|---|---|---|---|---|---|---|---|---|---|---|---|---|
| ConA A | | | | | | | | | | | | |
| B | | | | | | | | | | | | |
| C | | | | | | | | | | | | |
| D | | | | | | | | | | | | |
| RCA120 A | | | | | | | | | | | | |
| B | | | | | | | | | | | | |
| C | | | | | | | | | | | | |
| D | | | | | | | | | | | | |
| WGA A | | | | | | | | | | | | |
| B | | | | | | | | | | | | |
| C | | | | | | | | | | | | |
| D | | | | | | | | | | | | |
| BSA A | | | | | | | | | | | | |
| B | | | | | | | | | | | | |
| C | | | | | | | | | | | | |
| D | | | | | | | | | | | | |

METHOD OF MEASURING INTERACTION BETWEEN BIOMATERIAL AND SUGAR CHAIN, METHOD OF EVALUATING BIOMATERIAL IN SUGAR CHAIN SELECTIVITY, METHOD OF SCREENING BIOMATERIAL, METHOD OF PATTERNING BIOMATERIALS, AND KITS FOR PERFORMING THESE METHODS

CROSS REFERENCE TO RELATED APPLICATIONS

This application claims the benefit of Japanese Patent Application No. 340554/2006, filed Dec. 18, 2006, under 35 U.S.C. §119(a), the entire contents which are incorporated by reference herewith.

FIELD OF THE INVENTION

The present invention relates to a method of measuring an interaction between a biomaterial and a sugar chain, especially to a method of measuring an interaction between at least one biomaterial selected from the group consisting of protein viruses, cells, microorganisms, liposome, and micelles, and a sugar chain of a various kind, comprehensively, directly, digitally and promptly in real time without requiring labeling of samples. The present invention further relates to a method of evaluating the biomaterial in sugar chain selectivity, a method of screening the biomaterial, and a method of patterning the biomaterials, each of which utilizes the method of measuring the interaction, and to kits for performing these methods.

A method according to the present invention for measuring an interaction between a sugar chain(s) and at least one biomaterial selected from the group of consisting of proteins, viruses, cells, microorganisms, liposome, and micelles includes the step of bringing a solution containing the biomaterial in contact with a ligand carrier on which the sugar chain(s) is/are independently immobilized in such a manner that 1 to 500 kinds of the sugar chain(s) are immobilized per $cm^2$ on the ligand carrier.

Depending on the intensity of the interaction between the sugar chain of the ligand conjugate and the virus, a signal intensity varies which is caused by surface plasmon resonance, plasmon adsorption, or quartz crystal oscillation occurred as a result of the contact of the biomaterial with the ligand carrier. Thus, the interaction can be measured by measuring the signal intensity. Furthermore, by immobilizing such a number of kinds of the sugar chains per unit area, it becomes possible to perform a comprehensive measurement in which a plurality of sugar chains and the biomaterial are measured concurrently. Moreover, the measurement of the signal intensity can be performed on real time and needs no labeling. Therefore, it is possible to measure the interaction between the biomaterial and the sugar chains in a concurrently, comprehensively, non-labeling, and real-time manner. Moreover, the measurement in one time can be performed efficiently with low cost.

Moreover, it is possible to perform the measurement of the interaction between the biomaterial and the sugar chain sequentially in plural times by using the same ligand carrier without exchanging the ligand carrier. Therefore, the comprehensive measurement of the interaction between the biomaterial and the sugar chain can be carried out with good reproducibility.

Thus, the present invention is applicable to pharmaceutical industry, medical device industry, etc. which work on testing methods, diagnosing methods, preventing drugs or treating drugs of biomaterial-related diseases.

BACKGROUND OF THE INVENTION

Sugar chains are compounds in which sugars are bonded via glycoside bonding. There are infinite combinations of sugars considering kinds and sequences of sugars constituting the sugar chains. Therefore, there are a great variety of the sugar chains. It is known that sugar chains interact with various biomaterial such as viruses, cells, microorganisms, proteins, etc. Thus, the interactions of the sugar chains with the biomaterials largely influence physiological conditions of living organisms.

For example, it is known that infections of influenza virus, AIDS virus, and hepatitis B virus, which causes severe diseases in infected people, are initiated by interaction of these viruses with sugar chains in cell membranes of human cells. Different viruses interact with different sugar chains. This accounts for differences of virus infections in their infection routs and symptoms that they cause in humans.

For example, as disclosed in Virology, 1997, 227, 493-499, it is understood that isolated influenza virus strain interact with different sugar chains that are different in constituent sugars and sugar sequences. It is known that human-infectious influenza viruses generally interact with N-acetyl neuraminic acid $\alpha2,6$-galactose (Neu5Ac $\alpha2,6$ Gal) more strongly than N-acetyl neuraminic acid $\alpha2,3$-galactose (Neu5Ac $\alpha2,3$ Gal).

Therefore, comprehensive measurement on interactions of a virus with sugar chains is weighed heavily in developing strategies for prevention and remedy against the infection of the virus.

SUMMARY OF THE INVENTION

The present invention is accomplished in view of the aforementioned problems. An object of the present invention is to provide a method of screening or patterning a biomaterial in terms of their specificities to sugar chains by performing real-time and comprehensive measurement of an interaction between the sugar chain and the biomaterial with a very small amount of the biomaterial without labeling. In the present specification, the term "screening" is exchangeable with a term "identification", and the term "patterning" is exchangeable with a term "differentiation". Moreover, in the present invention the term "density" means a number of kinds of ligand conjugates immobilized per unit area of a support.

As a result of diligent studies, the inventors of the present invention found that it is possible to measure the interaction between the biomaterial (such as a virus, cell, microorganism, liposome, or micelle) and the sugar chain by bringing a solution containing the biomaterial in contact with a ligand carrier including a support whose surface includes a metal and a ligand conjugate on the surface, the ligand conjugate having a structure in which a linker compound having disulfide bonding (S—S bonding) or thiol group (SH group) is bonded with the sugar chain.

In one aspect, the invention is a method of measuring an interaction between a biomaterial and a sugar chain including the steps of contacting a solution containing the biomaterial with a ligand carrier, where the ligand carrier includes a support and a ligand conjugate, and measuring the interaction between the biomaterial and the sugar chain. The support includes a metal and the ligand conjugate includes a sugar chain bonded to a linker compound comprising a sulfur atom.

In some embodiments, there are 1 to 500 kinds of ligand conjugate immobilized on the ligand carrier per cm2.

In other embodiments, the biomaterial is a protein, virus, cell, microorganism, liposome, lipid, sugar chain, or micelle.

In another aspect, the invention is a method of evaluating the sugar selectivity of a biomaterial by measuring an interaction between the biomaterial and a sugar chain; and evaluating the interaction to measure the sugar selectivity of the biomaterial.

In yet another aspect the invention is a method of screening a target biomaterial by measuring an interaction between a target biomaterial and a sugar chain, measuring an interaction between a reference biomaterial and a sugar chain; and comparing the interactions to screen a target biomaterial.

In still yet another aspect, the invention is a method of patterning biomaterials by measuring interactions between each of two or more biomaterials and the sugar chain by performing the method of claim 1 and comparing results of the measurements to pattern the biomaterial.

The viruses can be influenza viruses, herpes virus, norovirus, HTLV-1 virus, AIDS virus, rotavirus, SARS virus, or Hepatitis B virus. The cells can be liver cells, or cancer cells of liver cancer, lung cancer, gastric cancer, small intestinal cancer, large intestinal cancer, pancreatic cancer, splenic cancer, or kidney cancer. The microorganisms can be *Escherichia coli, Helicobactor pylori, Pseudomonas aeruginosa*, lactic acid bacteria, or *Streptococci* spp.

In still yet another aspect, the invention is a kit for performing a method of measuring an interaction between a biomaterial and a sugar chain which contains a solution containing a biomaterial; and a ligand carrier, where the ligand carrier includes a support and a ligand conjugate. The support includes a metal and the ligand conjugate includes a sugar chain bonded to a linker compound comprising a sulfur atom.

A method according to the present invention is a method of measuring an interaction between a biomaterial and a sugar chain(s), the method including: bringing a solution containing the biomaterial in contact with a ligand carrier, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

With this arrangement, the ligand conjugate can be immobilized on the support via the metal-sulfur bonding easily. Moreover, because the sugar chain is contained in the ligand conjugate, the sugar chain can be indirectly immobilized on the support regardless of the kind of the sugar chain.

Moreover, the ligand conjugate is immobilized in the density as described above. This makes it possible to comprehensively measure the interaction between various sugar chains and the biomaterial by a single measurement. This reduces the amount of the biomaterial necessary for the measurement. Therefore, it is not necessary to prepare the biomaterial in a large quantity and it is possible to perform the measurement with a minute quantity. Moreover, this allows to perform a single measurement efficiently at a low cost.

Furthermore, the surface of the support has a (or is made of metal). This makes it possible to measure a signal intensity caused by surface plasmon resonance, plasmon absorption, or quartz crystal oscillation caused when the ligand carrier is brought in contact with the solution. The signal intensity varies depending of the intensity of the interaction between the sugar chain of the ligand conjugate and the biomaterial. Thus, the interaction can be digitally measured in one step by measuring the signal intensity. This allows accurate evaluation of the sugar chain selectivity of the biomaterial.

Moreover, the signal intensity is measure in real time by utilizing a physical phenomenon using a laser beam or the like. Therefore, it is possible to perform real-time and direct measurement without requiring labeling the biomaterial. Moreover, this can measure the interaction with high sensitivity, thereby reducing an amount of the biomaterial necessary for the measurement.

Moreover, it is possible to perform the measurement of the interaction between the biomaterial and the sugar chain sequentially in plural times by using the same ligand carrier without exchanging the ligand carrier. Therefore, the comprehensive measurement of the interaction between the biomaterial and the sugar chain can be carried out with good reproducibility.

A method according to the present invention is a method of evaluating a biomaterial in its sugar selectivity, the method including: measuring interactions between the biomaterial and sugar chain(s) by bringing a solution containing the biomaterial in contact with a ligand carrier; and finding specificity of the biomaterial to the sugar chain(s) from a result of the measurement, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

With this arrangement, by measuring the interaction between the biomaterial and the sugar chain, it is possible to evaluate how strong the interaction therebetween, thereby finding the intensity of the interaction between the biomaterial and the sugar chain. The ligand conjugate is immobilized on the support. This allows to find out the specificities of the biomaterial to various sugar chains. With this, it is possible to evaluate the biomaterial in its sugar chain selectivity comprehensively.

A method according to the present invention is a method of identifying a biomaterial, the method including: bringing a solution containing a target biomaterial and solutions respectively containing reference biomaterials in contact with a ligand carrier separately, so as to measure interactions between the respective biomaterials and a sugar chain(s); making a comparison between a result of the measurement of the solution containing the target biomaterial and results of the measurements of the solutions containing the reference biomaterials, so as to find a match among the results, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected, from the groups of viruses, cells, microorganisms, liposome, and micelles.

With this arrangement, it is possible to compare the result of the measurement of the solution containing the target biomaterial with the results of the measurements of the solutions of the reference biomaterials, thereby to find a match among the results. In other words, the target biomaterial can be compared with the reference biomaterials in terms of their specificities to the sugar chains thereby finding a reference biomaterial that is identical with the target biomaterial in terms of their specificities to the sugar chains. Thus, it is possible to identify the target biomaterial referring to its specificities to sugar chains.

Moreover, it is possible to perform the measurement of the interaction between the biomaterial and the sugar chain sequentially in plural times by using the same ligand carrier without exchanging the ligand carrier in which the ligand conjugate is immobilized in the above-mentioned density. Therefore, the comprehensive measurement of the interaction between the biomaterial and the sugar chain can be carried out with good reproducibility. As a result, it is possible to perform prompt and accurate comparison of the results of the measurements. Thus, it is possible to perform the identification of the biomaterial highly accurately.

A method according to the present invention is a method of patterning biomaterials, the method including: bringing a ligand carrier individually in contact with two or more solutions containing the different biomaterials, so as to measure interactions between the respective biomaterials and sugar chains; classifying the biomaterials by comparing results of the measurement, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

With this arrangement, it is possible that the biomaterials are compared in terms of their specificities to the sugar chain, and classified by their patterns in the specificities to the sugar chain. That is, they can be compared in terms of the strength of the interaction with the sugar chain, and classified in terms of the tendencies of the strength of the interaction. Thereby, the differentiation of the biomaterials can be performed.

Moreover, it is possible to perform the measurement of the interaction between the target or reference biomaterial and the sugar chain sequentially in plural times by using the same ligand carrier without exchanging the ligand carrier in which the ligand conjugate is immobilized in the above-mentioned density. Therefore, the comprehensive measurement of the interaction between the biomaterial and the sugar chain can be carried out with good reproducibility. As a result, it is possible to perform prompt and accurate comparison of the results of the measurements. Thus, it is possible to perform the differentiation of the biomaterial highly accurately.

A method according to the present invention is a method of measuring an interaction between a biomaterial and a sugar chain(s), the method including: bringing a solution containing the biomaterial in contact with a ligand carrier, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

With this arrangement, it is possible to perform real-time, comprehensive, direct and digital measurement of the interaction between the biomaterial with the sugar chain in one step without labeling. Thus, it is possible to evaluate the biomaterial in its sugar chain selectivity accurately. This method can perform the measurement without requiring a large amount of biomaterial. Thus, this method allows to measure the biomaterial with a minute quantity thereof.

A method according to the present invention is a method of evaluating a biomaterial in its sugar selectivity, the method including: measuring interactions between the biomaterial and sugar chain(s) by bringing a solution containing the biomaterial in contact with a ligand carrier; and finding specificity of the biomaterial to the sugar chain(s) from a result of the measurement, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

This allows to find out the specificities of the biomaterial to various sugar chains. With this, it is possible to evaluate the biomaterial in its sugar chain selectivity comprehensively.

A method according to the present invention is a method of identifying a biomaterial, the method including: bringing a solution containing a target biomaterial and solutions respectively containing reference biomaterials in contact with a ligand carrier separately, so as to measure interactions between the respective biomaterials and a sugar chain(s); making a comparison between a result of the measurement of the solution containing the target biomaterial and results of the measurements of the solutions containing the reference biomaterials, so as to find a match among the results, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

With this, it is possible to identify the target biomaterial highly accurately referring to its specificity to the sugar chain by comparing the target and reference biomaterials comprehensively in terms of the results of the measurements so as to find a match among the results.

A method according to the present invention is a method of patterning biomaterials, the method including: bringing a ligand carrier individually in contact with two or more solutions containing the different biomaterials, so as to measure interactions between the respective biomaterials and sugar chains; classifying the biomaterials by comparing results of the measurement, the ligand carrier including a support whose surface includes a metal, and a ligand conjugate(s) immobilized independently on the surface, the ligand carrier carrying the ligand conjugate(s) in such a density that 1 to 500 kinds of the ligand conjugate(s) is immobilized per $cm^2$, and each ligand conjugate having a structure in which a sugar chain is bonded with a linker compound having a sulfur atom, and the biomaterial being one selected from the groups of viruses, cells, microorganisms, liposome, and micelles.

With this, it is possible to differentiate the biomaterials highly accurately referring to its specificity to the sugar chain by comparing the biomaterials comprehensively in terms of the results of the measurements so as to classify the results.

Moreover, a kit according to the present invention for performing any of these method is a kit including a ligand carrier including a support whose surface includes a metal, and a ligand conjugate(s), each ligand conjugate having a structure in which a sugar chain is bonded with a linker compound having a sulfur atom.

This makes it possible to easily perform the method according to the present invention.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 2 illustrates centrifuged mixture solutions of sugar chain immobilized metal nano particles and influenza virus with sucrose added therein.

FIG. 3 illustrates results of measurement of interactions between sugar chains and proteins by using a surface plasmon resonance device.

DESCRIPTION OF THE EMBODIMENTS

Figure 1:
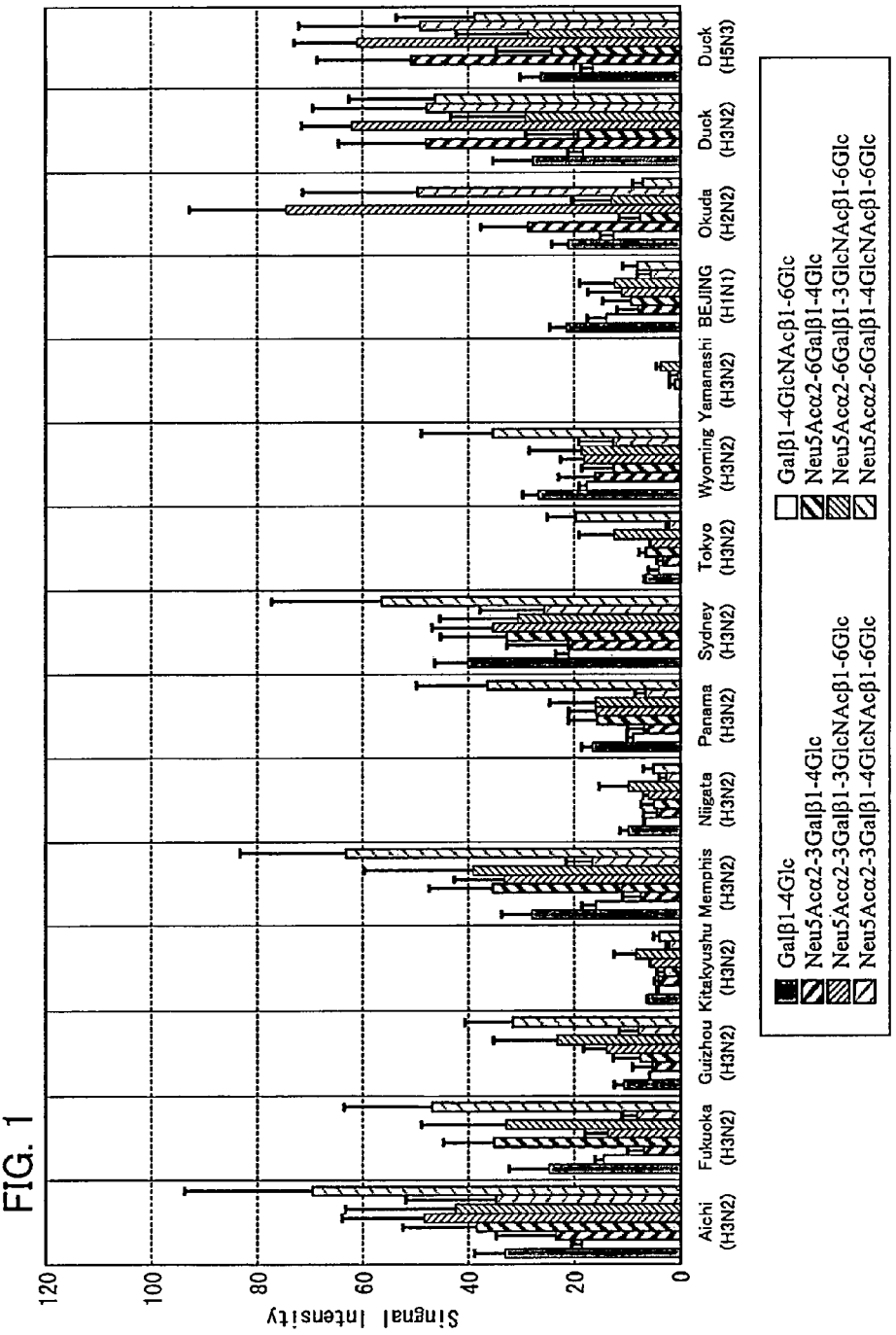
FIG. 1 is a graph illustrating results of measurements of interactions between sugar chains and influenza viruses by using a surface plasmon resonance device.
Figure 4:
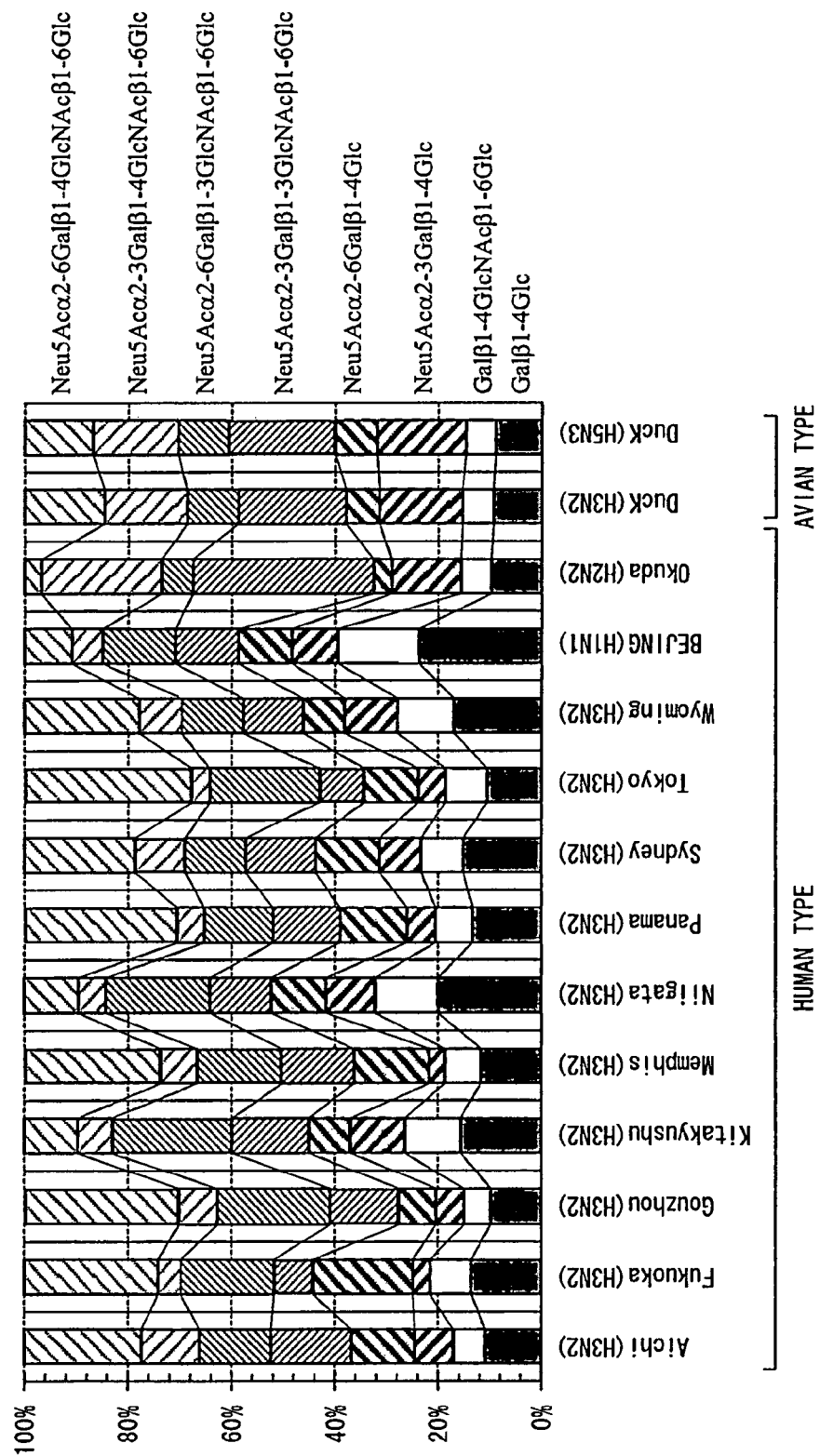
FIG. 4 is a graph illustrating ratios of reactions of 8 kinds of sugar chains to the influenza viruses where 100% is a sum of the levels (signal intensities illustrated in FIG. 1) of each reaction.

The present invention is described in more details. Note that the entire contents of all of the Non-Patent Literature documents and the Patent Documents cited in the present specification are incorporated hereby by reference.

<Support>

A support for use in the present invention includes metal on its surface. Examples of such a support encompass: a support made of a single material; a support including a substrate (first substrate) and a metal thin layer (first layer) on a surface of the substrate, the metal thin layer including at least one material that is different from a material of the substrate; a support including the first substrate, the first layer, and at least one intervening layer (second layer, third layer, etc.) therebetween.

The surface of the support is a portion at which a solution containing a biomaterial measurable or applicable in the present invention can be in contact with the support.

The metal may be Au, Ag, Cu, Al, Pt, aluminum oxide, $SrTiO_3$, $LaAlO_3$, $NdGaO_3$, $ZrO_2$, or the like. Moreover, the material of the first substrate may be glass, quartz, metal (e.g., Au, Ag, Cu, Al, Pt, aluminum oxide, $SrTiO_3$, $LaAlO_3$, $NdGaO_3$, $ZrO_2$, or the like), silicon (e.g., silicon oxide), a polymer resin (e.g., polyethylene terephthalate, polycarbonate), carbon (graphite), or the other compound. The support applicable in the present invention is not particularly limited in terms of its thickness. Usually, the first substrate is in the order of 0.1 mm to 30 mm, and preferably in the order of 0.1 mm to 2 mm.

The use of the support makes it possible to measure a strength of the interaction between the biomaterial and the sugar chain in a unit of a signal intensity produced by surface plasmon resonance, plasmon absorption, quartz crystal oscillation, or the like.

Especially, to measure the signal from the surface plasmon resonance, the support preferably has such an arrangement that the first substrate is made of a transparent material such as glass, a polymer resin, plastic, or the like, and the support includes the first layer, or the like arrangement. The first layer may be formed on the first substrate in any way. A conventionally known method such as vacuum vapor deposition, sputtering, electrolytic plating, immersion plating, metal foil lamination, chemical adsorption, or the like may be applied to provide the first layer on the first substrate. As one concrete example, a sensor chip described in the international publication, No. WO 2005/077965 may be cited.

Moreover, to measure the signal intensity caused by the plasmon absorption, the support is preferably arranged such that it is made of a single kind of metal. One example of such a support is metal nano particles. The metal nano particles are metal particles in colloid, which are preferably 1 to 200 nm in diameter. The metal nano particles may be prepared by any method. For example, the metal nano particles may be obtained by using a conventionally known method to dissolve metal chloride acid or its salt in a solvent such as methanol, water, a mixture thereof, or the like. Examples of the oxidized metal chloride or its salt encompass sodium gold chloride (III).

To measure the signal intensity caused by the quartz crystal oscillation, the support preferably includes a conventionally known quartz crystal oscillator. One example of such as quartz crystal oscillator is one described in Japanese patent application publication, Tokukai, No. 2005-84028.

<Linker Compound>

The linker compound applicable in the present invention is not particularly limited, provided that it contains a sulfur atom and is capable of bonding with a sugar chain. One example of the linker compound bondable with the sugar chain is a linker compound having a functional group such as an amino group. The sulfur atom may be present in the form of a disulfide bonding (S—S bonding) or a thiol group (SH group). One concrete example of such linker compounds is a linker compound described in international publication No. WO 2005/077965.

One concrete example of the linker compounds applicable in the present invention is a linker compound having a structure represented by General Formula (1):

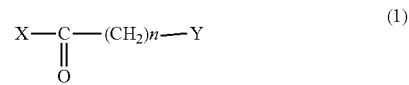

$n = 0-6$ where Y is a structure containing a sulfur atom.

Moreover, X in General Formula (1) of the linker compound is a branched structure section that includes 1 to 4 hydrocarbon chains each of which has a terminal aromatic amino group with or without a carbon-nitrogen bond in its main chain. With the linker compound of this structure, an assembly of plural sugar chains can be arranged on the surface of the support. Further, the present of the terminal aromatic amino group makes it easy to introduce the sugar chain. Furthermore, there is no particular limitation as to n in the General Formula (1), provided that n is not less than 0 but not more than 6.

For example, the linker compound represented in General Formula (1) is produced by a condensation reaction of thioctic acid and a terminal of an aromatic amino group.

<Sugar Chain>

The sugar chain applicable in the present invention is a compound in which sugars are bonded via glycoside bonding. The sugars may be any sugars that have a reducing terminal. Preferable examples of such sugars are sugars having sialic acid or a sulfate group.

Examples of the sugars having a reducing terminal encompass: maltose, lactose, panose, cellobiose, melibiose, mannno oligosaccharide, chitooligosaccharide, laminari oligosaccharide, and the like. The sugar having sialic acid is not particularly limited. Examples of the sugar having sialic acid are silalyllactose and the like.

The sugar chain may be a mono-component oligosaccharide consisting of the same sugars, or a complex oligosaccharide consisting of various sugars and derivatives thereof. The oligosaccharide may be an artificially synthesized saccharide or a natural saccharide that is isolated and purified from a natural product. Moreover, the oligosaccharide may be obtained by breaking down a polysaccharide.

For example, the sugar chain may be Glc, GlcNAc, Gal, Glcα1-4Glc, Glcα1-4Glcα1-4Glc, Glcα1-6Glc, Glcα1-6Glcα1-6Glc, Glcβ1-3Glcβ1-3Glc, Glcβ1-4Glc, Glcβ1-6Glc, Galα1-6Glc, Galα1-4Galβ1-4Glc, Galβ1-3GalNAcα1-6Glc, Galβ1-4GlcNAcβ1-6Glc, Galβ1-4Glc, Galβ1-4-[Fucα1-2]GlcNAcβ1-3Galβ1-4Glc, Manα1-2Man, Manα1-3Manα1-6Man, Manα1-6Man, Fucα1-2Galβ1-4Glc, Fucα1-6Glc, Fucβ1-6Glc, Xylβ1-6Glc, GlcNAcα1-6Glc, GlcNAcβ1-4GlcNAc, GlcNAcβ1-6Glc, GlcNAcβ1-3Galβ1-4GlcNAcβ1-3Galβ1-4Glc, GalNAcα1-6Glc, GalNAcβ1-3Gal, Neu5Acα2-3Galβ1-4Glc, Neu5Acα2-3Galβ1-4GlcNAc, Neu5Acα2-3Galβ1-3GlcNAcβ1-6Glc, Neu5Acα2-3Galβ1-4GlcNAcβ1-6Glc, Neu5Acα2-6Galβ1-4Glc, Neu5Acα2-6Galβ1-3GlcNAcβ1-6Glc, Neu5Acα2-6Galβ1-4GlcNAcβ1-6Glc, GlcNS6Sα1-4IdoA2Sβ1-6Glc, Galβ1-4GlcGalβ1-4GlcNAcβ1-6Glc, Neu5Acα2-3Galβ1-4Glc, Neu5Acα2-6Galβ1-4Glc, Neu5Acα2-3Galβ1-3GlcNAcβ1-6Glc, Neu5Acα2-6Galβ1-3GlcNAcβ1-6Glc, Neu5Acα2-3Galβ1-4GlcNAcβ1-6Glc, Neu5Acα2-6Galβ1-4GlcNAcβ1-6Glc, GlcAβ1-3GalNAc4Sβ1-6Glc, GlcAβ1-3GalNAc6Sβ1-6Glc, GlcAS2β1-3GalNAc6Sβ1-6Glc, GlcAβ1-3GalNAc4S6Sβ1-6Glc, GlcNS6Sα1-4IdoA2Sα1-6Glc, GlcNSα1-4IdoA2Sα1-6Glc, GlcNS6Sα1-4GlcA2Sβ1-6Glc, GlcNSα1-4GlcAβ1-6Glc, or the like.

The following explains the abbreviations used in this specification: "Glc" denotes Glucose; "Gal" denotes Galactose; "Man" denotes Mannose; "Fuc" denotes Fucose; "Xyl" denotes Xylose, "NAc" denotes N-Acetyl; "Ido" denotes Idose; "Neu5Ac" denotes N-Acetylneuraminic acid; "GlcA" denotes Glucuronic acid; "IdoA" denotes Iduronic acid; and "S" in the chemical formula of the sugar chains denotes sulfonyl (sulfate group). For example, "4S" in GlcAβ1-3GalNAc4Sβ1-6Glc denotes 4-O-sulfonyl.

Moreover, "α" and "β" in the chemical formula of the sugar chains indicate that the hydroxyl group of the sugar on the reducing-terminal side is bonded with the hydroxyl group its adjacent sugar, forming an α or β steric structure. For example, "α1-4" means that 1-position hydroxyl group of the sugar on the reducing-terminal side is bonded with 4-position hydroxyl group of the adjacent sugar, forming an α steric structure.

<Ligand Conjugate>

The ligand conjugate applicable in the present invention is a structure in which a linker compound described in <Linker Compound> is bonded with a sugar chain described in <Sugar Chain>. The linker compound and the sugar chain may be bonded by any method, which may be a conventionally known method. For example, in case the linker compound has the structure represented by General Formula (1), the linker compound has an amino group. Thus, the linker compound can be easily bonded with a sugar having a reducing terminal, via reducing amination. More specifically, the ligand conjugate may have a structure represented by General Formula (2) or (3), or the like structure.

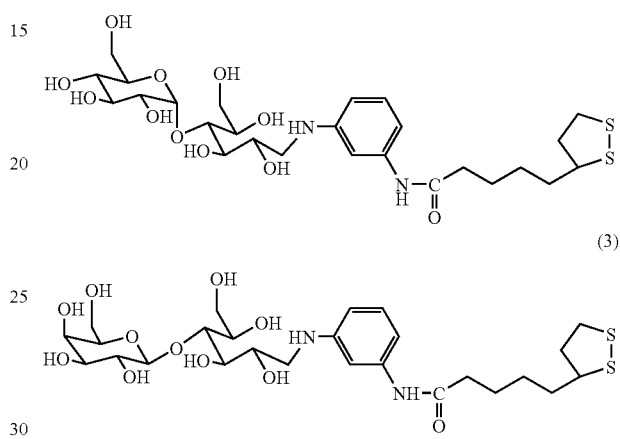

(2)

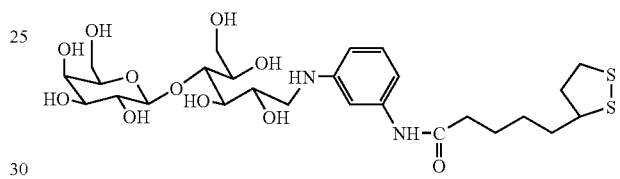

(3)

<Ligand Carrier>

The ligand carrier applicable in the present invention has such a structure that the ligand conjugate is immobilized on the support.

In one embodiment, a method according to the present invention is a method of measuring an interaction between a biomaterial and a sugar chain(s), the method comprising: bringing a solution containing the biomaterial in contact with a ligand carrier, the ligand carrier including a support whose surface includes a metal, and a ligand conjugate(s) immobilized independently on the surface, the ligand carrier carrying the ligand conjugate(s) in such a manner that 1 to 500 kinds of the ligand conjugate(s) is immobilized per $cm^2$, and each ligand conjugate having a structure in which a sugar chain is bonded with a linker compound having a sulfur atom, and the biomaterial being at least one selected from the groups of proteins, viruses, cells, microorganisms, liposome, and micelles.

The arrangement, the "ligand conjugate(s) immobilized independently on the surface, the ligand carrier carrying the ligand conjugate(s) in such a manner that 1 to 500 kinds of the ligand conjugate(s) is immobilized per $cm^2$" means that the ligand conjugates are immobilized on the surface of the support such that 1 to 500 kinds of the ligand conjugate(s) are present per 1 $cm^2$ of the surface, and that when plural ligand conjugates are immobilized in respective areas, the ligand conjugate in one area do not overlap with the ligand conjugate in the other area.

For example, in the later-described Example, the ligand conjugate are spotted on an Au-deposited glass substrate of 1.8 cm×1.8 $cm^2$. A ligand conjugate in one spot does not overlap with a ligand conjugate in another spot. That is, the ligand conjugate in one spot is immobilized on the surface on the support independently of the ligand conjugate in another spot.

Because the ligand conjugates of 1 to 500 kinds are immobilized per $cm^2$ of the support, one or plural kinds of ligand conjugates may be immobilize per $cm^2$ of the support. In case where plural kinds of ligand conjugates are immobilize per $cm^2$ of the support, all the kinds of the ligand conjugates immobilized per $cm^2$ are different, or some of the plural kinds may be identical. For example, in the later-described Example, 48 kinds of ligand conjugates are spotted in 96 areas of the support of 1.8 cm×1.8 cm.

Note that the term "ligand conjugate" in the present specification has a structure a linker compound described in <Linker Compound> and a sugar chain described in <Sugar Chain, as described in <Ligand conjugate>. Therefore, ligand conjugates having different linker compounds or different sugar chains may be regarded as different ligand conjugates.

With this arrangement in which the ligand conjugate(s) are immobilized independently on the surface, the ligand carrier carrying the ligand conjugate(s) in such a manner that 1 to 500 kinds of the ligand conjugate(s) is immobilized per $cm^{2"}$, it is possible to measure the interaction between the biomaterial and sugar chain as a reaction between a liquid phase (a solution containing the biomaterial) and a solid phase (the sugar chains immobilized independently). Thus, one sample of the solution containing the biomaterial is enough to comprehensively confirm the reaction between the biomaterial and the sugar chains comprehensively. This makes it possible to perform the screening and patterning of the biomaterials efficiently.

Without wishing to be bound by theory, we believe that the advantages of the invention in part arise from the fact that the sugar chain is present as the solid phase immobilized on the support. This prevents the sugar chain from being dissolved into the liquid phase flowing over the support. Thus, the sugar chain and the biomaterial can be easily separated and the biomaterial can be collected each other after measuring their interaction. The collected biomaterial can be reused for measurement of the sugar chain immobilized on another support. That is, regardless of the number of the sugar chains to measure, only one sample of the biomaterial is sufficient. Thus, it is possible to obtain much information with a sample of a small quantity. This makes it possible to perform very efficient measurement of the interaction. This makes it possible to perform the screening and patterning of the biomaterials with a sample of a small quantity.

The immobilization of the ligand conjugate on the support may be carried out in any way. The ligand conjugate has such a structure that the linker compound having a sulfur atom is bonded with the sugar chain. Further, the support has a metal surface. Thus, a metal-sulfur (S) bond is easily formed when the ligand conjugate and the support is in contact with each other. This allows to immobilize the ligand conjugate on the surface of the support.

For example, the immobilization may be carried out by spotting, on the metal surface of the support, a ligand solution in which the ligand conjugate is dissolved in a solvent.

Especially, use of a conventionally known spotter device (e.g., Toyobo Co. Ltd.: MultiSPRinter spotter) makes it possible to immobilize the ligand conjugates independently on the metal surface of the support in such a high density as preferably 1 to 50 kinds/$cm^2$, and more preferably 1 to 500 kinds/$cm^2$. Note that the range "1 to 500 kinds" is inclusive of 1 kind and 500 kinds. The more kinds of the ligand conjugates immobilized in the higher density, the more kinds of results a single measurement obtains. This reduces the amount of the biomaterial in the measurement. Thus, the immobilization of such a number of kinds of the ligand conjugates per unit area on the support makes it possible to measure the biomaterial with a minute amount.

In this case, the ligand solution is spotted in an amount preferably in a range of 1 nL to 1000 nL and further preferably in a range of 5 nL to 30 nL.

To check whether or not such a number of kinds of the ligand conjugates are immobilized per unit area on the support can be carried out by testing the ligand carrier with a later-described surface plasmon resonance device so as to measure surface plasmon resonance at a spot in which the ligand carrier is not present and at the spot in which the ligand carrier is immobilized.

Moreover, any solvent may be used as the solvent above. For example, the solvent may be methanol, water, dimethylacetamide (DMAc), glycerol, or a mixture solvent of two or more of them. Moreover, it is sufficient that a contact time be in the order of 0.5 hours to 12 hours. Ligand conjugate concentration in a range of 1 µM to 1 mM is sufficient for the ligand solution. Furthermore, it is preferable to keep the support in a humidity of 50% to 80%, and preferably in a humidity of 70% to 80% while the ligand solution and the support are in contact with each other. This prevents the evaporation of the ligand solution while the ligand solution and the support are in contact with each other. The humidity control can be performed in any way. For example, the humidity can be controlled by using a conventional humidifier or the like.

Moreover, the immobilization of the ligand conjugate on the metal nano particles may be performed in any way. For example, the immobilization may be attained by mixing a solution of the metal nano particles with the ligand conjugate. More specifically, the immobilization of the ligand conjugate on the metal nano particles can be carried out by adding the solution containing the metal nano particles to a solution containing the ligand conjugate and stirring the mixture. It is sufficient that the stirring time be of the order of 30 seconds. The ligand conjugate concentration in the ligand solution is preferably in a range of 1 µM to 10 mM, and more preferably in a range of 10 µM to 1 mM. Hereinafter, the ligand carrier prepared by immobilizing the ligand conjugate on the metal nano particles will be referred to as sugar chain-immobilized metal nano particles.

If a metal salt is contained in the solution, it is preferable that the metal be reduced with a reducing agent before mixing the solution with the ligand conjugate. This makes it easier to bond the metal with the ligand conjugate. The reducing agent is not limited to a particular one, and may be, for example, sodium boron hydride, citric acid and a salt thereof, ascorbic acid and a salt thereof, phosphor, tannic acid and a salt thereof, ethanol, hydrazine, or the like.

There is no particular limitation in a dispersing medium in the solution containing the metal and in the solvent of the solution containing the ligand conjugate. For example, methanol, water, and the mixture solvent thereof, etc. may be cited as the dispersing medium and the solvent. Moreover, the ligand carrier obtained by the mixing may be dialyzed to remove a salt of a low molecule or the like therefrom. In this way, it is possible to obtain a ligand carrier stable in the solution.

There is no particular limitation as to a mixing ratio of (i) the metal to prepare the sugar chain immobilized metal nano particles, (ii) reducing agent, and (iii) ligand conjugate. In case the metal is a chloroauric acid and chloroaurate thereof, a final concentration of the chloroauric acid and chloroaurate thereof is preferably in a range of 0.5 mM to 10 nM, and more preferably in a range of 1 mM to 5 mM.

A final concentration of the reducing agent in the solution is more concentrated in mol concentration than Au ions, preferably by 3 to 10 times, and more preferably by 4 to 5 times.

Moreover, A final concentration of the ligand conjugate in the solution is preferably in a range of 10 µM to 1000 µM, and more preferably in a range of 50 µM to 150 µM.

<Biomaterial>

From the result of Examples and this knowledge, it is expected that the measuring method of the present invention is capable of measuring not only the interactions between one compound and one compound, such as between a sugar chain and a protein, but also interactions between one compound and plural compounds such as between a sugar chain and at least one constituent selected from the group consisting of lipids, sugar chains, and proteins. On this account, it is expected that the measuring method be applicable not only to the detection of the interaction between the sugars and proteins, but also patterning of virus strains. That is, the method according to the present invention can recognize and distinguish different biomaterials having proteins identical in antibody type.

For example, proteins, viruses, cells, microorganisms, liposome, micelles, etc. can be the biomaterials. More concrete examples of the viruses encompass-influenza viruses, herpes virus, norovirus, HTLV-1 virus, AIDS virus, rotavirus, SARS virus, and Hepatitis B virus.

More specifically, examples of the protein encompass animal lectins, plant lectins, enzymes, growth factors, intercellular signal transfer factors, gene regulatory factors, extracelluar matrix construction components, antibodies, and the like.

More specifically, the cells may be cancer cells and non-cancer cells. Among the cancer cells, the method of the present invention is preferably applicable to measure cancer cells derived from liver cancer, brain tumor, lung cancer, gastric cancer, small intestinal cancer, large intestinal cancer, pancreatic cancer, splenic cancer, kidney cancer, or the like. The method of the present invention is especially preferably applicable to measure a cancer cell selected from the group of liver cancer, lung cancer, gastric cancer, small intestinal cancer, large intestinal cancer, pancreatic cancer, splenic cancer, and kidney cancer.

Meanwhile, as to non-cancer cells, the method of the present invention is preferably applicable to measure liver cells etc., for example.

Moreover, as of the microorganisms, the measuring method of the present invention is preferably applicable to measure *Escherichia coli, Helicobactor pylori, Pseudomonas aeruginosa*, lactic acid bacteria, *Streptococci* sp. etc. Of *E. coli*, the measuring method of the present invention is particularly preferably applicable to O-157. The liposome and micelles may be prepared from a living sample or artificially produced, provided that the liposome and micelles contain a sugar chain. There is no particular limitation as to the preparation of the liposome and micelles from the living sample. For example, a living sample such as cells, tissues, etc. may be broken down in a solution containing a surfactant by supersonic treatment or the like, thereby to extract a liposome or a micelle in the solution from the living sample.

The artificial preparation of liposome is not limited to a particular method. For example, a liposome may be artificially prepared by stirring and mixing a solution which contains a lipid and a sugar chain with which a liposome of phospholipid or the like can be formed.

As to the biomaterial concentration in the solution containing the biomaterial, it is sufficient that the concentration be in a range of 0.1 ng/ml to 10 mg/ml, and it is preferably that the concentration be in a range of 0.1 µg/ml to 1 mg/ml. Moreover, when the biomaterial is virus, the virus concentration is preferably in a range of 1 to $10^{10}$ pfu/ml, and more preferably in a range of 10 to 100 pfu/ml. It is possible to find pfu by a well known method such as TCID 50 (50% Tissue Culture Infection Dose) or the like. Further, when the biomaterial is an influenza virus, the influenza virus concentration is preferably in a range of 1 to 1000 HAU, and more preferably in a range of 10 to 100 HAU. Here, HAU is a Hemagglutinating Unit, that is, a unit indicative of hemagglutinating property of the influenza virus with red blood cells. It is possible to measure HAU by hemagglutinating reaction with a 0.5% avian blood cell solution.

When the biomaterial is cells or microorganisms, the concentration of the cells or microorganisms is preferably in a range of $10^3$ cells/ml to $10^{10}$ cells/ml, and more preferably in a range of $10^5$ cells/ml to $10^7$ cells/ml. The concentration of the cells or microorganisms can be measured by a well known method such as by using a cell counter or the like.

The measuring method of the present invention is highly sensitive because it measures a signal intensity caused by surface plasmon resonance, plasmon absorption or quartz crystal oscillation. This gives such an advantage that the measurement only requires an extremely small amount of the biomaterial.

The virus can be prepared by a conventionally known method. For example, a virus to measure is inoculated in a culturing cell and incubate at 37° C. for 2 to 4 days. After that, a culture supernatant is laminated on a lamination of 30% and 60% sucrose solutions different in specific gravity. Then, this fluid lamination is subjected to ultracentrifugation (24,000 rpm, 90 min, 15° C.). Then, the 30%/60% fractions are collected. In this way, a solution containing the virus can be prepared.

Here, the culture cell may be any culture cell to which the virus can infect. For example, if the virus is an influenza virus, an amnion of an embryonated hen egg for intramembranous inoculation, a MDCK cell, or the like may be used as the culture cell appropriately.

Moreover, the cells may be prepared by a conventionally known method. For example, the cells to measure may be incubated in a known culture liquid under incubation conditions suitable for the cells, and then collected in a desired concentration. The collection of the cells is not particularly limited to a particular method. For floating cells, centrifugation can be adopted to collect the cells in the desired concentration. Moreover, as to adherent cells, the cells may be removed from a petri dish by using enzyme digestion such as with trypsin or by a physical method such as pipetting, and then centrifuged to collect the cells in the desired concentration.

Moreover, the microorganisms may be prepared in a conventionally known method. For example, the microorganisms to measure may be incubated in a known culture liquid under incubation conditions suitable for the microorganisms, and then collected by centrifugation or the other method.

By diluting, with a solution, the biomaterial such as the virus, cells, microorganisms, or the like thus prepared, the "solution containing the biomaterial" in the concentration can be prepared. The solution to add may be a conventionally known buffer solution such as a PBS (Phosphate Buffered Saline) solution (pH 7.4), tris buffer solution, or the like. Moreover, the solution may contain sodium chloride, magnesium chloride, EDTA or a salt thereof, EGTA or a salt thereof, and/or a surfactant such as Tween 20, Triton X, CHAPS or the like. Surfactant concentration in the solution is preferably in a range of 0.001 to 10%, and more preferably in a range of 0.005% to 5%.

<Measurement of Interaction Between Biomaterials and Sugar Chains>

The measuring method according to the present invention is not particularly limited, provided that the method can measure the interaction between the biomaterial and the sugar chain. For example, the interaction between the biomaterial and the sugar chain can be measured by measuring a signal intensity produced by surface plasmon resonance, plasmon absorption, or quartz crystal oscillation caused when the ligand carrier touches the biomaterial by bringing the ligand conjugate in a contact with the solution containing the biomaterial. The signal intensity varies depending on the strength of the interaction between the biomaterial and the sugar chain. That is, in this specification, what is meant by the measurement of the interaction between the biomaterial and the sugar chain is to measure a strength of at least one kind of bonding selected from the group consisting of a hydrogen bond, a hydrophobic bond, an ionic bond, and a van der waals bond between the biomaterial and the sugar chain.

The interaction between the biomaterial and the sugar chain may be measured by using a solution containing one kind of biomaterial. Alternatively, the interaction between the biomaterial and the sugar chain may be measured by using two or more solutions each containing one kind of biomaterial thereby to obtain readings for the respective solutions individually.

In the following, embodiments of the measurements of the interactions between the biomaterials and the sugar chains according to the present invention are explained. In the embodiments, the magnitudes of signals from the surface plasmon resonance, plasmon absorption, and the quartz crystal oscillations are measured respectively to measure the interaction.

<Surface Plasmon Resonance>

The signal intensity from the surface plasmon resonance can be measured by any methods including conventional known methods. For example, the signal intensity from the surface plasmon resonance can be measured in real time by using a surface plasmon resonance device later described.

That is, a degree of the surface plasmon resonance caused as a result of the interaction between the biomaterial and the sugar chain can be measured in the unit of the signal intensity by using the surface plasmon resonance device. The surface plasmon resonance varies depending on the strength of the interaction between the sugar chain of the ligand conjugate and the biomaterial. Thus, the strength of the interaction can be measured in the unit the signal intensity.

The surface plasmon resonance is measured by the signal intensity in real time by utilizing a physical phenomenon by using a laser beam or the like. This makes it possible to perform real-time direct measurement in which the labeling the biomaterial is not necessary. Moreover, it is possible to measure the interaction with high sensitivity. As a result, it is possible to perform the measurement with a smaller amount of the solution containing the biomaterial. Further, it is preferable to digitalize the strength of the interaction after the measurement. The digitalization makes it easier to screen or pattern the biomaterial.

Specifically, this measurement is carried out as follows. The ligand carrier is set in the surface plasmon resonance device. It is preferable that a running buffer flow over the surface of the ligand carrier in the surface plasmon resonance device. This is because the ligand carrier can be in contact with the solution containing the biomaterial by replacing the running buffer by flowing the solution containing the biomaterial. The surface plasmon will occur if an interaction occurs between the biomaterial in the solution and the sugar of the ligand conjugate immobilized on the ligand carrier when the ligand carrier is brought in contact with the solution. The signal intensity that represents the degree of the surface plasmon resonance is measured. In this way, the interaction between the biomaterial and the sugar chain is measured.

The biomaterial concentration in the solution containing the biomaterial is preferably as described in <Biomaterial> above. As to how much the solution containing the biomaterial is to be added, the amount of the solution is sufficiently in a range of 10 to 5000 µl, and more preferably in a range of 50 to 300 µl.

One example of the surface plasmon resonance device is MultiSPRinter (Toyobo Co. Ltd.).

There is no particular limitation as to how many kinds of the ligand carriers are set in the surface plasmon resonance device. Only one ligand carrier may be set or plural ligand carriers may be set. In case the plural ligand carriers are set, the ligand carriers may be identical with or different from each other. What is meant by the wording "the ligand carriers are different" is such differences that the ligand conjugates immobilized in the ligand carriers are different, that the supports contained in the ligand carrier are different, and the like differences. What is meant by the wording the "ligand conjugates are different" is such differences that the linker compounds or the sugar chains contained in the ligand conjugates are different.

The running buffer may be a conventionally known buffer solution such as the PBS solution (pH7.4), tris buffer solution, or the like. Moreover, the running buffer may contain sodium chloride, magnesium chloride, EDTA or a salt thereof, EGTA or a salt thereof, and/or a surfactant such as Tween 20, Triton X, CHAPS or the like. The surfactant concentration in the buffer solution is preferably in a range of 0.001% to 10%, and more preferably in a range of 0.005% to 5%.

In the present embodiment, it is preferable that the ligand carrier be washed with a washing solution before the ligand carrier is brought in contact with the solution containing the biomaterial. This removes impurities attached on the ligand carrier before the ligand carrier is brought in contact with the solution containing the biomaterial. The washing solution is not limited to a particular one. For example, the washing solution may be (i) a basic aqueous solution such as sodium hydroxide solution, potassium hydroxide solution, etc, (ii) acidic solution such as hydrochloric acid solution, sulfuric acid solution, etc., (iii) a buffer solution containing the surfactant mentioned above, (iv) or the other liquid.

The basic or acid solution may be in any concentration, provided that the ligand carrier (especially, the sugar chain) will not be denatured by the solution at the concentration. The concentration is preferably in a range of 0.1 mM to 100 mM and more preferably in a range of 1 mM to 10 mM.

In the present embodiment, it is preferable that the measurement of the interaction between the biomaterial and the sugar chain be carried out by measuring the surface plasmon resonance in sequentially plural times.

The wording "carried out by measuring in sequentially plural times" means such a process that measurement of the interaction between one biomaterial and the sugar chain is carried out by bringing the ligand carriers in contact with a solution contain the one biomaterial, and then measurement of the interaction between another biomaterial and the sugar chain is sequentially carried out by bringing the ligand carriers in contact with a solution contain the another biomaterial.

In this case, it is preferable that, after previous measurement of a previous biomaterial is finished, the ligand carrier be washed with the washing solution before a solution containing a next biomaterial is flown for next measurement. In this way, the previous biomaterial bonded to the sugar chain in the previous measurement can be washed away. The next biomaterial to be brought in contact with the sugar chain next may contain the same biomaterial as the previous biomaterial or different from the previous biomaterial.

This method makes it possible to measure the interaction between plural biomaterials and a sugar chain by using the same ligand carrier. This allows to compare results of the measurements highly accurately in a short time. Thus, this makes it possible to screen or pattern the biomaterials as described later.

<Plasmon Absorption>

The measurement of the plasmon absorption is not particularly limited, provide that it includes the step of causing the interaction between the sugar chain and the biomaterial by mixing the solution containing the sugar chain-immobilized metal nano particles with the solution containing the biomaterial, so as to produce a product of sugar chain-biomaterial interaction.

The "solution containing the sugar chain-immobilized metal nano particles" is a solution in which the sugar chain-immobilized metal nano particles are dispersed in a liquid. As long as the sugar chain-immobilized metal nano particles are contained, the solution may contain any substance such as a salt. For example, the liquid may be water or a buffer solution such as PBS solution, tris buffer solution, or the like.

The mixing of the solution containing the sugar chain-immobilized metal nano particles with the solution containing the biomaterial is not particularly limited to any method, provided that the mixing allows the interaction between the sugar chain and the biomaterial. For example, the mixing may be carried out by adding the solution containing the sugar chain-immobilized metal nano particles to a series of dilutions of the biomaterial on a microplate or Eppendorf tube, and leaving the series of dilutions for a certain period.

More specifically, the solution containing the sugar chain-immobilized metal nano particles has a final concentration is preferably in a range of 0.5 mM to 10 mM, and more preferably in a range of 1 mM to 5 mM. The solution containing the biomaterial has the biomaterial concentration as described in <Biomaterial>. The solution containing the sugar chain-immobilized metal nano particles and the solution containing the biomaterial in such concentrations are mixed. As to the amount of the solution containing the sugar chain-immobilized metal nano particles to add is not particularly limited. It is preferable that the amount of the solution containing the sugar chain-immobilized metal nano particles to add be in a range of 10 to 1000 µl. As to the amount of the solution containing the biomaterial to add is not particularly limited. It is preferable that the amount of the solution containing the biomaterial to add be in a range of 10 to 1000 µl.

The "product of sugar chain-biomaterial interaction" is an coagulated material produced as a result of specific bonding between the sugar and the biomaterial due to the interaction therebetween. The measurement of the plasmon absorption can be observed by observing the product of sugar chain-biomaterial interaction visually, which represents the interaction between the sugar chain and the biomaterial. When the sugar and the biomaterial do not interact with each other, the product of sugar chain-biomaterial interaction will not be produced.

One example of the method of observing a coagulation reaction so as to measure an interaction between substances is a latex agglutination method using an antigen-antibody reaction, or the like method (see "Development and evaluation of bio diagnostic agents, and companies thereof", CMC technical library 146, CMC publishing Co., Ltd., p 92-97, p 109-113). The latex agglutination method immobilizes an antibody on a surface of a latex and makes a series of dilutions of antibody using a 96-well microplate, finds a most dilution to allow the coagulation, and compare a result of the measurement of the most dilution with a result of reference solution. In case where the sugar chain immobilized Au nano particles, the plasmon absorption is measured as a change in absorption of a certain wavelength (the signal intensity caused by the plasmon absorption). The use of this method makes it possible to digitalize the interaction between the biomaterial and the sugar chain.

The measurement of the signal intensity caused by the plasmon absorption allows the interaction between the sugar chain and the biomaterial without labeling. In terms of not requiring a pretreatment, this method is more simple than the method requiring such labeling. Furthermore, this method is free from such a problem that the labeling effect largely influences reproducibility of the measurement. Thus, with this method, the measurement can be performed with good reproducibility. Moreover, the interaction between the sugar chain and the biomaterial can be observed visually. Thus, no particular device is necessary. Thus, the interaction between the sugar chain and the biomaterial can be measured and digitalized very easily and economically.

Moreover, again in the present embodiment, the interaction between the sugar chain and the biomaterial is preferably measured subsequently in plural time by the plasmon absorption measurement, as in <Surface Plasmon Resonance>. This subsequent measurements can be carried out as described in <Surface Plasmon Resonance>.

<Quarts Crystal Oscillation>

The method of measuring the unit of the signal intensity caused by the quartz crystal oscillation is not limited to a particular method. For example, a method described in Japanese Patent Application Publication, Tokukai, No. 2005-84028, etc.

For example, the ligand conjugate is immobilized on a metal portion of a quartz crystal oscillator, thereby to prepare a ligand carrier. The immobilization can be performed by the method described in <Ligand Carrier>. After that, the solution containing the biomaterial is brought in contact with the ligand carrier. A resonance frequency (the signal intensity caused by the quarts crystal oscillation) caused thereby is measured. The magnitude of the resonance frequency varies depending on the interaction between the biomaterial and the sugar chain. Thus, real-time measurement of the resonance frequency makes it possible to measure the interaction of the biomaterial and the sugar chain in real time.

As to the biomaterial concentration in the solution containing the biomaterial, the concentration is preferably in the concentration described in <Biomaterial>. Moreover, the amount of the solution containing the biomaterial to add is not particularly limited. However, the amount of the solution containing the biomaterial to add is preferably in a range of 10 to 1000 µl, and more preferably in a range of 50 to 500 µl.

Moreover, again in the present embodiment, the interaction between the sugar chain and the biomaterial is preferably measured subsequently in plural time by measuring the signal intensity caused by the quartz crystal oscillation, as in <Surface Plasmon Resonance>. This subsequent measurements can be carried out as described in <Surface Plasmon Resonance>.

<Measurement of Interactions Between Sugar Chains and Viruses>

In preferred embodiments, as described in later-described Examples, the method of the present invention can divide influenza viruses having similar H3N2 protein into strains by identifying their specificities to different sugar chains. Note that "H3" denotes hemagglutinin of type 3, and "N2" denotes neuraminidase of type 2. Both are determined by using antibodies.

The specificity patterns of influenza virus strains to the sugar chain are not predictable and follow no pattern, such as proportionally or inverse-proportionally. The wording "specificity to the sugar chain" refers to the affinity between the biomaterial and the sugar chain.

For example, comparison of A/Fukuoka/C29/85(H3N2) and A/Guizhou/54/89(H3N2) based on their specificity pattern to sugar chains shows that both influenza viruses interacted with a sugar chain "Neu5Acα2-6Galβ1-4GlcNAcβ1-6Glc" with similar strengths. By contrast, binding to a sugar chain "Neu5Acα2-6Galβ1-4Glc", A/Fukuoka/C29/85 (H3N2) showed strong interaction, while there is limited interaction with A/Guizhou/54/89(H3N2). This result suggests that the specificity pattern to the sugar chains is not dependent on the level of expression of the H3N2 proteins that are determined using antibodies, or that the protein has been mutated at a site at which the mutation cannot be distinguished with antibody.

In preferred embodiments, this method is used to evaluate the binding of the viruses of the following sugar chains. Among these sugar chains, Neu5Acα2-6Galβ1-4Glc, Neu5Acα2-6Galβ1-3GlcNAcβ1-6Glc, and Neu5Acα2-6Galβ1-4GlcNAcβ1-6Glc are sugar chains that positively interacts with influenza viruses infectious to human being typically.

Moreover, Neu5Acα2-3Galβ1-4Glc, Neu5Acα2-3Galβ1-3GlcNAcβ1-6Glc, and Neu5Acα2-3Galβ1-4GlcNAcβ1-6Glc are sugar chains that positively interacts with influenza viruses infectious to Aves and Equidae typically.

Moreover, Galβ1-4Glc and Galβ1-4GlcNAcβ1-6Glc are sugar chains that are negative in the interaction with the influenza viruses.

By measuring interactions between an influenza virus and these sugars by using the ligand carrier, it is possible to find out which one of human, Aves, and Equidae the influenza virus is infectious to.

It is said that herpes virus interacts with sulfated sugar chain (JOURNAL OF VIROLOGY October 2000, P 9106-9114, JOURNAL OF VIROLOGY June. 1996, P 3461-3469). Thus, used as the positively interacting sugar chains were GlcNS6Sα1-4IdoA2Sα1-6Glc, GlcNSα1-4IdoA2Sα1-6Glc, GlcNS6Sα1-4GlcA2Sβ1-6Glc, and GlcNSα1-4GlcAβ1-6Glc, which are parts of the structure of heparin or heparan sulfate. Similarly, used as the positively interacting sugar chains were GlcAβ1-3GalNAc6Sβ1-6Glc, GlcA2Sβ1-3GalNAc6Sβ1-6Glc, and GlcAβ1-3GalNAc4S6Sβ1-6Glc, which are parts of the structure of chondroitin.

As the negatively interacting sugar chains, neutral sugars, sialic acid, such as the sugar chains listed in Table 2 were used.

By using the ligand carrier, it is possible to measure the interaction between herpes viruses and the sugar chains, thereby to analyze the types of the herpes viruses.

<Method of Evaluating Sugar Chain Selectivity of Biomaterial>

The method according to the present invention for evaluating the biomaterial in its sugar chain selectivity is for evaluating the biomaterial in its specificity to a sugar chain. Here, what is meant by the wording "its specificity to a sugar chain" is a tendency in the strength of the interaction between the biomaterial and the sugar chain. That is, by measuring the interaction between the biomaterial and the sugar chain, it is possible to find how strong the interaction therebetween, thereby finding the tendency in the strength of the interaction between the biomaterial and the sugar chain. With this, it is possible to evaluate the biomaterial in its sugar chain selectivity.

Therefore, the method according to the present invention for evaluating the biomaterial in its sugar chain selectivity includes the steps of (i) measuring interaction between a biomaterial and a sugar chain by bringing a solution containing the biomaterial in contact with a ligand carrier, and (ii) finding specificity of the biomaterial to the sugar chain from a result of the measurement.

The solution containing the biomaterial is not particularly limited, provided that the solution is as described in <Biomaterial>.

The ligand carrier is not particularly limited, provided that the ligand carrier is as described in <Ligand Carrier>. It is possible to evaluate the biomaterial in terms of its specificities to more ligand conjugate-bonded sugars by using a ligand carrier that carries more ligand conjugates thereon. This makes it possible to perform comprehensive evaluation.

It is preferably that the interaction between the unlabeled biomaterial and the sugar chain be carried out by measuring the signal intensity caused by the surface plasmon resonance, plasmon absorption, or quartz crystal oscillation. In this way, it is possible to digitalize the signal intensity. Thus, the readings of the measurement of the interaction between the biomaterial and the sugar chain can be digitalized. The digitalization allows to make a numerical comparison to find how strong the interaction between the biomaterial and the sugar chain is. Therefore, with this method, it is possible to easily and accurately evaluate the biomaterial in its specificity to the sugar chain.

Moreover, the evaluation in the sugar chain specificity may be absolute or relative evaluation. The absolute evaluation is to evaluate the biomaterial in its specificity to the sugar chain without comparing it with a specificity of another biomaterial to the sugar chain. The relative evaluation is to evaluate the biomaterial in its specificity to the sugar chain by comparing it with a specificity of another biomaterial to the sugar chain.

The evaluation of the biomaterial in its specificity to the sugar chain makes it possible to screen or pattern the biomaterial.

<Method of Screening Biomaterial>

Biomaterial screening according to the present invention is to screen a target biomaterial in terms of its specificity to a sugar by evaluating the target biomaterial in its sugar selectivity. Here, the term "target biomaterial" means a biomaterial to be screened.

Therefore, the method according to the present invention for screening a biomaterial includes the steps of (i) bringing a solution containing a target biomaterial and solutions respectively containing reference biomaterials in contact with a ligand carrier separately, so as to measure interactions between the respective biomaterials and a sugar chain(s), (ii) making a comparison between a result of the measurement of the solution containing the target biomaterial and results of the measurements of the solutions containing the reference biomaterials, so as to find a match among the results.

The "solution containing the target biomaterial" is an aqueous solution containing the biomaterial to be screened. The "biomaterial to be screened" may be a biomaterial, which is unknown itself, or a biomaterial which is known itself, but whose specificity to the sugar chain is unknown. Moreover, the "solution containing the reference biomaterial" is an aqueous solution that contains a biomaterial whose specificity to the sugar chain is known for the screening of the target biomaterial.

The ligand carrier is not particularly limited, provided that the ligand carrier is as described in <Ligand Carrier>. It is possible to evaluate the biomaterial in terms of its specificities to more ligand conjugate-bonded sugars by using a ligand carrier that carries more ligand conjugates thereon. This makes it possible to perform more accurate screening.

In the step of "bringing a ligand carrier in contact individually with a solution containing the target biomaterial or solutions respectively containing reference biomaterials so as to measure interactions between the target and reference biomaterials and the sugar chain", the solution containing the target biomaterial and the solution containing the reference biomaterial may be respectively brought in contact with the ligand carriers of the same structure, or the solution containing the target biomaterial and the solution containing the reference biomaterial may be sequentially (one after the other) brought in contact with a ligand carrier.

The latter allows more prompt and accurate comparison, and thus is preferable to the former. As to an order in which the solutions of the biomaterials are brought in contact with the ligand carrier, there is no particular limitation. The solution containing the target biomaterial may be brought into contact with the ligand carrier after the solution containing the reference biomaterial.

By measuring the signal intensity caused by the surface plasmon resonance, plasmon absorption, or quarts crystal oscillation occurred by bringing the ligand carrier in contact with the solution containing the target biomaterial and the solution containing the reference biomaterial, it is possible to digitally measure the intensity of the interaction of the target or reference biomaterial with the sugar chain.

As to the step of making a comparison between a result of the measurement with the solution containing the target biomaterial and results of the measurements with the solutions containing the reference biomaterials, so as to find a match among the results, this step is preferably embodied such that the target biomaterial is compared with the reference biomaterials in terms of theirs specificities to the sugar chain, thereby to find a reference biomaterial that is identical with the target biomaterial in terms of the specificity. That is, by comparing the target biomaterial and the reference biomaterials in terms of the strengths of theirs interaction with the sugar chain, and find a reference biomaterial that is identical with the target biomaterial in terms of strengths of theirs interaction with the sugar chain, it is possible to find which reference biomaterial is identical with the target biomaterial. In this way, it is possible to screen the target biomaterial.

<Method Patterning Biomaterial>

The biomaterial patterning according to the present invention is to classify the biomaterial in terms of its specificity to a sugar by evaluating its sugar specificity described above.

Therefore, the method according to the present invention for patterning the biomaterial includes the step of bringing two or more kinds of solutions each containing a biomaterial in contact with a ligand carrier so as to measure interactions of the biomaterials and a sugar chain, and comparing results of the measurements so as to perform classification.

In the step of "bringing two or more kinds of solutions each containing a biomaterial in contact with a ligand carrier so as to measure interactions of the biomaterials and a sugar chain", the solutions may be respectively brought in contact with ligand carriers of the same structure, or the solutions may be sequentially brought in contact with a ligand carrier.

The latter allows more prompt and accurate comparison, and thus is preferable to the former. The two or more kinds of biomaterials may be identical with or different from each other, but it is preferable that they be different from each other in terms of patterning.

The ligand carrier is not particularly limited, provided that it is as described in <Ligand Carrier>. It is possible to evaluate the biomaterial in terms of its specificities to more ligand conjugate-bonded sugars by using a ligand carrier that carries more ligand conjugates thereon. This makes it possible to perform more detailed patterning.

By measuring the signal intensity caused by the surface plasmon resonance, plasmon, absorption, or quarts crystal oscillation occurred by bringing the ligand carrier with the solutions containing the biomaterials, it is possible to measure the interaction between the biomaterials and the sugar chain.

In the step of "comparing results of the measurements so as to perform classification", it is preferable that the biomaterials are compared in terms of their specificities to the sugar chain, and classified by their patterns in the specificities to the sugar chain. That is, they can be compared in terms of the strength of the interaction with the sugar chain, and classified in terms of the tendencies of the strength of the interaction. Thereby, the patterning of the biomaterials can be performed.

<Kit>

A kit for performing the method according to the present invention includes the ligand carrier as described in <Ligand Carrier> above. Therefore, the method according to the present invention can be performed with the kit. Moreover, the kit may includes a biomaterial, a running buffer described above, an agent such as the washing solution, a surface plasmon resonance device or the like, for measuring the signal intensity caused by the surface plasmon resonance, the plasmon absorption, or the quartz crystal oscillation. With this arrangement, the method according to the present invention can be performed easily.

For example, the sugar chain may be at least one sugar chain selected from the group consisting of Galβ1-4Glc, Galβ1-4GlcNAcβ1-6Glc, Neu5Acα2-3Galβ1-4Glc, Neu5Acα2-6Galβ1-4Glc, Neu5Acα2-3Galβ1-3GlcNAcβ1-6Glc, Neu5Acα2-6Galβ1-3GlcNAcβ1-6Glc, Neu5Acα2-3Galβ1-4GlcNAcβ1-6Glc, Neu5Acα2-6Galβ1-4GlcNAcβ1-6Glc, GlcAβ1-3GalNAc6Sβ1-6Glc, GlcAS2β1-3GalNAc6Sβ1-6Glc, GlcAβ1-3GalNAc4S6Sβ1-6Glc, GlcNS6Sα1-4IdoA2Sα1-6Glc, GlcNSα1-4IdoA2Sα1-6Glc, GlcNS6Sα1-4GlcA2Sβ1-6Glc, and GlcNSα1-4GlcAβ1-6Glc. That is, at least one of the sugar chains selected from the group may be used as the sugar chain carried by the ligand carrier.

The present invention may be expressed as follows.

The method according to the present invention is preferably arranged such that the structure of the linker compound is represented by:

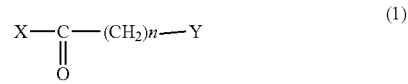

(1)

$n = 0\text{-}6$ where X is a branched structure section that includes 1 to 4 hydrocarbon chains each of which has a terminal aromatic amino group with or without a carbon-nitrogen bond in its main chain, and Y is a hydrocarbon structure having the sulfur atom, and n is not less than 0 but not more than 6.

In this arrangement, the linker compound contains 1 to 4 aromatic amino groups in its molecule. Moreover, the amino groups can be easily bonded with a sugar chain having a reducible terminal by reducing amination. Therefore, the use of the linker compound makes it possible to have a ligand conjugate in which 1 to 4 sugar chains are bonded with one linker compound.

The method according to the present invention is preferably arranged such that the viruses are influenza viruses, herpes virus, norovirus, HTLV-1 virus, AIDS virus, rotavirus, SARS virus, and Hepatitis B virus, the cells are liver cancer, lung cancer, gastric cancer, small intestinal cancer, large intestinal cancer, pancreatic cancer, splenic cancer, kidney cancer, and liver cells and the microorganisms are *Escherichia coli, Helicobactor pylori, Pseudomonas aeruginosa*, lactic acid bacteria, and *Streptococci* spp.

With this arrangement, it is possible to measure the interaction between these biomaterials and a sugar chain. Moreover, it is possible to identify or differentiate these biomaterials. As a result, it is possible to identify the sugar chain interactive with these biomaterials. Furthermore, it is possible to identify sugar chains commonly interactive with the these biomaterials.

The method according to the present invention is preferably arranged such that the biomaterial is an influenza virus, and the sugar chain(s) is at least one selected from the group consisting of: Galβ1-4Glc, Galβ1-4GlcNAcβ1-6Glc, Neu5Acα2-3Galβ1-4Glc, Neu5Acα2-6Galβ1-4Glc, Neu5Acα2-3Galβ1-3GlcNAcβ1-6Glc, Neu5Acα2-6Galβ1-3GlcNAcβ1-6Glc, Neu5Acα2-3Galβ1-4GlcNAcβ1-6Glc, and Neu5Acα2-6Galβ1-4GlcNAcβ1-6Glc.

With this arrangement, it is possible to perform a comprehensive, real-time and direct measurement of the interaction between the influenza virus and the sugar chains.

Among these sugar chains, Neu5Acα2-6Galβ1-4Glc, Neu5Acα2-6Galβ1-3GlcNAcβ1-6Glc, and Neu5Acα2-6Galβ1-4GlcNAcβ1-6Glc are sugar chains that positively interacts with influenza viruses infectious to human being typically. Moreover, Neu5Acα2-3Galβ1-4Glc, Neu5Acα2-3Galβ1-3GlcNAcβ1-6Glc, and Neu5Acα2-3Galβ1-4GlcNAcβ1-6Glc are sugar chains that positively interacts with influenza viruses infectious to Aves and Equidae typically. Moreover, Galβ1-4Glc and Galβ1-4GlcNAcβ1-6Glc are sugar chains that are negative in the interaction with the influenza viruses.

Therefore, it is possible to study an influenza virus on its host specificity by measuring the interactions of the influenza virus with any of the sugar chains by using a ligand carrier having the sugar chains. Moreover, this makes it possible to perform influenza virus identification or differentiation.

Moreover, a kit according to the present invention for performing any of these method is a kit including a ligand carrier including a support whose surface includes a metal, and a ligand conjugate(s), each ligand conjugate having a structure in which a sugar chain is bonded with a linker compound having a sulfur atom.

With this arrangement in which the kit includes the ligand carrier, it is possible to easily perform the method according to the present invention.

The kit according to the present invention is preferably arranged such that the sugar chain(s) is at least one selected from the group consisting of: Galβ1-4Glc, Galc 1-4GlcNAcβ1-6Glc, Neu5Acα2-3Galβ1-4Glc, Neu5Acα2-6Galβ1-4Glc, Neu5Acα2-3Galβ1-3GlcNAcβ1-6Glc, Neu5Acα2-6Galβ1-3GlcNAcβ1-6Glc, Neu5Acα2-3Galβ1-4GlcNAcβ1-6Glc, and Neu5Acα2-6Galβ1-4GlcNAcβ1-6Glc.

In this arrangement, the ligand carrier includes the sugar chains that positively interacts with influenza viruses infectious to human being typically, the sugar chains that positively interacts with influenza viruses infectious to Aves and Equidae typically, and the sugar chains that are negative in the interaction with the influenza viruses. When the method with this arrangement is applied to a case where the biomaterial is an influenza virus, it is possible to measure the interactions of the influenza virus and the sugar chains concurrently, economically, comprehensively and real time.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLE

In the following, the present invention is described in further details referring to Examples, which are not to limit the present invention.

Example 1

Preparation of Ligand Conjugate

Ligand conjugates immobilized on ligand carriers used in Example 3 or Example 5 were prepared in the same manner as described in the international publication No. WO 2005/077965.

Firstly, a linker compound containing thioctic acid and m-phenylenediamine was prepared. After that, the linker compound was reacted respectively with the sugar chains listed in Table 1 and 2, thereby carrying out reducing amination.

Tables 1, 2, 3 and 4 respectively show the sugar chains of ligand conjugates immobilized on ligand carriers used in Example 3, Example 5, Example 4, and Example 6.

TABLE 1

| SUGAR CHAINS BONDED TO LIGAND CONJUGATE OF EXAMPLE 1 |
| --- |
| Galβ1-4Glc |
| Galβ1-4GlcNAcβ1-6Glc |
| Neu5Acα2-3Galβ1-4Glc |
| Neu5Acα2-6Galβ1-4Glc |
| Neu5Acα2-3Galβ1-3GlcNAcβ1-6Glc |
| Neu5Acα2-6Galβ1-3GlcNAcβ1-6Glc |
| Neu5Acα2-3Galβ1-4GlcNAcβ1-6Glc |
| Neu5Acα2-6Galβ1-4GlcNAcβ1-6Glc |

TABLE 2

| SPOT POSITION IN FIG. 3 | SUGAR CHAINS BONDED TO LIGAND CONJUGATE OF MEASUREMENT EXAMPLE |
| --- | --- |
| A1 | Glc* |
| A2 | GlcNAc* |
| A3 | Gal* |
| A4 | Glcα1-4Glc* |
| A5 | Glcα1-4Glcα1-4Glc* |
| A6 | Glcα1-6Glc* |

TABLE 2-continued

| SPOT POSITION IN FIG. 3 | SUGAR CHAINS BONDED TO LIGAND CONJUGATE OF MEASUREMENT EXAMPLE |
|---|---|
| A7 | Glcα1-6Glcα1-6Glc* |
| A8 | Glcβ1-3Glcβ1-3Glc* |
| A9 | Glcβ1-4Glc* |
| A10 | Glcβ1-6Glc* |
| A11 | Galα1-6Glc* |
| A12 | Galα1-4Galβ1-4Glc* |
| B1 | Galβ1-3GalNAcα1-6Glc* |
| B2 | Galβ1-4GlcNAcβ1-6Glc* |
| B3 | Galβ1-4Glc* |
| B4 | Galβ1-4[Fucα1-2]GlcNAcβ1-3Galβ1-4Glc* |
| B5 | Manα1-2Man* |
| B6 | Manα1-3Manα1-6Man* |
| B7 | Manα1-6Man* |
| B8 | Fucα1-2Galβ1-4Glc* |
| B9 | Fucα1-6Glc* |
| B10 | Fucβ1-6Glc* |
| B11 | Xylβ1-6Glc* |
| B12 | GlcNAcα1-6Glc* |
| C1 | GlcNAcβ1-4GlcNAc* |
| C2 | GlcNAcβ1-6Glc* |
| C3 | GlcNAcβ1-3Galβ1-4GlcNAcβ1-3Galβ1-4Glc* |
| C4 | GalNAcα1-6Glc* |
| C5 | GalNAcβ1-3Gal* |
| C6 | Neu5Acα2-3Galβ1-4Glc* |
| C7 | Neu5Acα2-3Galβ1-4GlcNAc* |
| C8 | Neu5Acα2-3Galβ1-3GlcNAcβ1-6Glc* |
| C9 | Neu5Acα2-3Galβ1-4GlcNAcβ1-6Glc* |
| C10 | Neu5Acα2-6Galβ1-4Glc* |
| C11 | Neu5Acα2-6Galβ1-3GlcNAcβ1-6Glc* |
| C12 | Neu5Acα2-6Galβ1-4GlcNAcβ1-6Glc* |
| D1 | GlcNS6Sα1-4IdoA2Sβ1-6Glc* |
| D2 | Heparin |
| D3 | — |
| D4 | — |
| D5 | — |
| D6 | — |
| D7 | — |
| D8 | — |
| D9 | — |
| D10 | — |
| D11 | — |
| D12 | — |

※ NON-CYCLIC SUGAR CHAINS ARE DENOTED WITH *

TABLE 3

SUGAR CHAINS BONDED TO LIGAND CONJUGATE OF EXAMPLE 2

Galβ1-4Glc*
Neu5Acα2-6Galβ1-4GlcNAcβ1-6Glc*

※ NON-CYCLIC SUGAR CHAINS ARE DENOTED WITH *

TABLE 4

SUGAR CHAINS BONDED TO LIGAND CONJUGATE OF EXAMPLE 3

GlcNS6Sα1-4IdoA2Sα1-6Glc
GlcNSα1-4IdoA2Sα1-6Glc
GlcNS6Sα1-4GlcA2Sβ1-6Glc
GlcNSα1-4GlcAβ1-6Glc
GlcAβ1-3GalNAc4S6Sβ1-6Glc

Example 2

Preparation of Ligand Carrier

Ligand carriers used in Example 3 or Example 5 were prepared as follows. Firstly, an Au-deposited glass (SPR-200: Toyobo Co. Ltd.) was washed with a small-size UV/O3 cleaner (BioForce Nanosciences, Inc.) for 20 minutes.

After that, ligand conjugate solutions of 500 μM were prepared, each of which contained one ligand conjugate that was prepared in Example 1 and had a sugar chain listed in Table 1 or 2. The ligand conjugate solutions are introduced to 96-well plate by adding 20 μl in each well. Next, the plate was placed in a MultiSPRinter auto spotter device (Toyobo Co. Ltd.). Then, the ligand conjugate was spotted approximately in 10 nl on the Au-deposited glass substrate. This spotter was capable of forming, at maximum, 8×12 spots on the Au-deposited glass substrate of 1.8 cm×1.8 cm square shape.

After the spotting of the ligand conjugate solution, the Au-deposited glass substrate was allowed to stand in humidity of the order of 70 to 80% for 12 hours, thereby immobilizing the ligand conjugate on the surface of the Au deposition glass.

Moreover, the ligand carriers used in Example 4 were prepared as follows. Sodium chloroaurate (III) of 1 mM and sodium boron hydride were mixed with vigorously stirring thereby to reduce Au ions. To the thus prepared Au nano particle solution, the ligand conjugate produced in Example 1 and listed in Table 1 was added to make up 100 μM. The solution was mixed vigorously stirred, thereby obtaining a colloid solution of non-refined sugar-chain immobilized metal nano particles.

Next, the colloid solution of the non-refined sugar-chain immobilized metal nano particles was transferred to a dialysis tube (MWCO:3,500) and subjected to dialysis with water and PBS-T (0.05%), thereby purifying the colloid solution to a solution of sugar-chain immobilized metal nano particles (ligand carriers). Ultraviolet visible absorption spectrum of the solution of the sugar-chain immobilized metal nano particles was measured to find that its maximum absorption wavelength was 525 nm.

Example 3

Measurement of Interaction between Sugar Chain and Isolated Influenza Virus Strain <Preparation Method of Influenza Virus>
This Example used the following isolated influenza virus strains classified with the class names as follows:
A/Aichi/2/68(H3N2), A/Fukuoka/C29/85(H3N2), A/Guizhou/54/89(H3N2), A/Kitakyusyu/159/93(H3N2), A/Memphis/1/71(H3N2), A/Niigata/102/81(H3N2), A/Panama/2007/99(H3N2), A/Sydney/5/97(H3N2), A/Tokyo/6/73(H3N2), A/Wyoming/3/2003(H3N2), A/Yamanashi/2/77(H3N2), A/Beijing/262/95(H1N1), A/Okuda/57 (H2N2), A/duck/HK/24/79(H3N2), and A/duck/HK/313/4/78(H5N3).

These influenza virus was provided from Hyogo College of Medicine.

The class names show Type/Isolation Location and Species/Isolation Number/Isolation Year (Antigenic Types of hemagglutinin (HA) and neuraminidase (NA)).

Solutions of the isolated influenza virus strains were prepared as follows. MDCK cells were incubated in a MEM plate. In the plate, an isolated influenza virus strain was inoculated and incubated at 37° C. for 2 to 4 days. After that, a pre-solution of the isolated influenza virus strain was prepared from the plate by using a conventionally known method. The pre-solution was laminated on a lamination of 30% and 60% sucrose solutions different in specific gravity. Then, this fluid lamination was subjected to ultracentrifugation (24,000 rpm, 90 min, 15° C.). Then, resultant 30%/60% fractions were collected. In this way, a solution containing the isolated influenza virus strain was prepared. The solution containing the isolated influenza virus strain was analyzed in its hemagglutination Unit (HAU) by observing hemagglutinating reaction with a 0.5% avian blood cell solution.

<Measurement of Interaction Between Sugar Chain and Isolated Influenza Virus Strain>

Interactions between the ligand carriers prepared in Example 2 and the isolated Influenza virus strains were measured in the following manner by using a surface plasmon resonance device (Toyobo Co. Ltd.: MultiSPRinter).

Firstly, the ligand carrier was set in the surface plasmon resonance device. Then, the ligand carrier was washed with NaOH aqueous solution of 10 mM. Before the solution of the isolated influenza virus strain was added, the solution flowing over the surface of the ligand carrier was replaced with Phosphate Buffered Saline (PBS) solution containing 0.05% Tween 20 (hereinafter, referred to as "PBS-T"). The PBS solution had pH 7.4. The measurement was carried out at room temperatures.

A solution of the isolated influenza virus strain was prepared with the PBS solution to the concentration of 100 HAU. The thus prepared solution was flown over the surface of the ligand carrier at a flow rate of 150 µl/min for 5 min.

If this causes interaction between the isolated influenza virus strain and one sugar chain of one ligand conjugate immobilized on one ligand carrier, a surface plasmon resonance will occur at a spot position of the ligand conjugate. Therefore, real-time measurement of the signal intensity (brightness) caused by the surface plasmon resonance allows real-time measurement of the interaction.

FIG. 1 is a graph of the digitalized results of the measurement of the interactions between the sugar chains and the isolated influenza virus strains.

FIG. 1 demonstrates that the isolated influenza virus strains showed different specificities to the sugar chains respectively.

Furthermore, FIG. 1 shows that the influenza viruses of the same A type and H3N2 type could be further classified into (i) influenza virus strains that had similar patterns in specificities to the sugar chains, as A/Aichi/2/68(H3N2) and A/Sydney/5/97(H3N2), and (ii) influenza virus strains that were weak in the interaction with the sugar chains, as A/Kitakyusyu/159/93(H3N2), A/Niigata/102/81(H3N2), A/Tokyo/6/73(H3N2), and A/Yamanashi/2/77(H3N2).

Therefore, Example 3 demonstrates that it is possible to measure the interaction between an isolated influenza strain (s) and sugar chains thereby to carry out influenza virus screening or patterning.

Example 4

In a tube, 500 µl of the sugar chain-immobilized nano particles prepared in Example 2 and 200 HAU of an influenza virus were mixed. Then, the mixture solution thus prepared was left for 30 min. Into the mixture solution, sucrose solutions of 35%, 40%, 45%, 50%, and 60% were added in 1.5 ml each in this order. Then, the tube was centrifuged at 24000 rpm for 90 min at 15° C.

FIG. 2 illustrates the centrifuged mixtures solutions of the sugar chain-immobilized metal nano particles and an influenza virus with sucrose added therein. "SGNP" indicates the sugar chains immobilized on the sugar chain-immobilized metal nano particles, and "virus" indicates whether the influenza virus was added therein or not. "Side" shows side views of the centrifuged tubes, and "bottom" shows bottom views of the centrifuged tubes.

FIG. 2 demonstrates that a coagulation product was observed at the bottom of the tube of the sample which underwent interaction between the influenza virus and the sugar chain and subsequent centrifugation. On the other hand, no coagulation product was observed at the bottoms of the samples in which either the sugar chain-immobilized metal nano particles or influenza virus was not introduced, or in which no interaction occurred between the influenza virus and the sugar chain.

Therefore, Example 4 demonstrates that a sugar chain-influenza virus interaction product to coagulate is produced by the interaction between the influenza virus and the sugar chain as a result of mixing the sugar chain-immobilized metal nano particles and the influenza virus.

Example 5

Measurement of Interaction Between Sugar Chain and Protein

An interaction between the ligand carrier prepared in Example 2 and a protein was measured by the following method using the surface plasmon resonance device (Toyobo Co., Ltd: MultiSPRinter).

Firstly, the ligand carrier was set in the surface plasmon resonance device. After that, the ligand carrier was washed with NaOH aqueous solution of 10 mM for approximately 10 min. Before adding the protein, the solution flowing over the surface of the ligand carrier was replaced with PBS-T. The measurement was carried out at room temperatures.

In an Eppendorf tube, a 2.0 µM solution of the protein was prepared with the PBS-T. Then, the solution was flown over the surface of the ligand carrier (sugar chain immobilized measurement medium) at a flow rate of 150 µl/min for 5 min.

If this causes interaction between the protein and one sugar chain of one ligand conjugate immobilized on one ligand carrier, a surface plasmon resonance will occur at a spot position of the ligand conjugate. Therefore, real-time measurement of the signal intensity (brightness) caused by the surface plasmon resonance allows real-time measurement of the interaction.

The present Example measured the following proteins: concanavalin A (Con A), *Ricinus Communis* agglutinin (RCA120), and wheat germ agglutinin (WGA). Moreover, bovine fetal serum albumin (BSA) was measured as a negative control.

FIG. 3 illustrates results of the measurements of the interactions between the proteins and sugar chains by using the surface plasmon resonance device.

According to FIG. 3, spot positions with increased brightness were observed on the ligand carrier in the use of concanavalin A (Con A). This showed that concanavalin A (Con A) interacted with the sugar chains immobilized at the spot positions.

Furthermore, spot positions with increased brightness were observed on the ligand carrier in the use of *Ricinus Communis* agglutinin (RCA 120) and wheat germ agglutinin (WGA). This showed that *Ricinus Communis* agglutinin (RCA 120) and wheat germ agglutinin (WGA) interacted with the sugar chains immobilized at the spot positions.

In addition, it was found that the spot positions at which the brightness was increased were specific to the respective proteins.

Meanwhile, it was observed that the use of bovine serum albumin (BSA) showed an increase in brightness at none of the spot positions in which the ligand carrier was present, even though the BSA was at the same concentration as the others.

Therefore, the present Example confirmed that it was possible to measure the interaction of a sugar chain and a protein and evaluate the protein in terms of its specificity to the sugar chain.

Example 6

Measurement of Interaction between Sugar Chain and Isolated Herpes Virus Strain

<Preparation of Herpes Virus>

In the present Example, isolated herpes virus strains were used, which were classified as classification names, HSV-1 (CHR-3 Strain) and HSV-2 (MS strain) respectively. The isolated herpes virus strains were provided from Hyogo College of Medicine.

The isolated herpes virus strains were prepared as follows. In an MEM plates in which VeroE6 cells were cultured, an isolated herpes virus strain was inoculated and incubated at 37° C. for 2 to 4 days. After that, a pre-solution of the isolated herpes virus strain was prepared from the plates by a conventionally known method.

The pre-solution was laminated on a lamination of 30% and 60% sucrose solutions different in specific gravity. Then, this fluid lamination was subjected to ultracentrifugation (24,000 rpm, 90 min, 15° C.). Then, resultant 30%/60% fractions were collected. In this way, a solution containing the isolated herpes was prepared. Titre of the solution containing the isolated herpes virus strain was evaluated in PFU (Plaque-Forming Unit) to VeroE6 cells.

<Measurement of Interaction Between Sugar Chains and Isolated Herpes Virus Strain>

Interactions between the ligand carriers prepared in Example 2 and the isolated herpes virus strains were measured in the following manner by using a surface plasmon resonance device (Toyobo Co., Ltd: MultiSPRinter).

Firstly, the ligand carrier was set in the surface plasmon resonance device. Then, the ligand carrier was washed with NaOH aqueous solution of 10 mM. Before the solution of the isolated herpes virus strain was added, the solution flowing over the surface of the ligand carrier was replaced with Phosphate Buffered Saline (PBS) solution of pH 7.4 (hereinafter, referred to as "PBS-T"). The measurement was carried out at room temperatures.

A solution of the isolated herpes virus strain was prepared with PBS-T at an isolated herpes virus strain concentration of 2.4 to 59.2 µg/ml. The thus prepared solution was flown over the surface of the ligand carrier at a flow rate of 150 µl/min for 5 min.

If this causes interaction between the isolated herpes virus strain and one sugar chain of one ligand conjugate immobilized on one ligand carrier, a surface plasmon resonance will occur at a spot position of the ligand conjugate. Therefore, real-time measurement of the signal intensity (brightness) caused by the surface plasmon resonance allows real-time measurement of the interaction.

Figure 5:
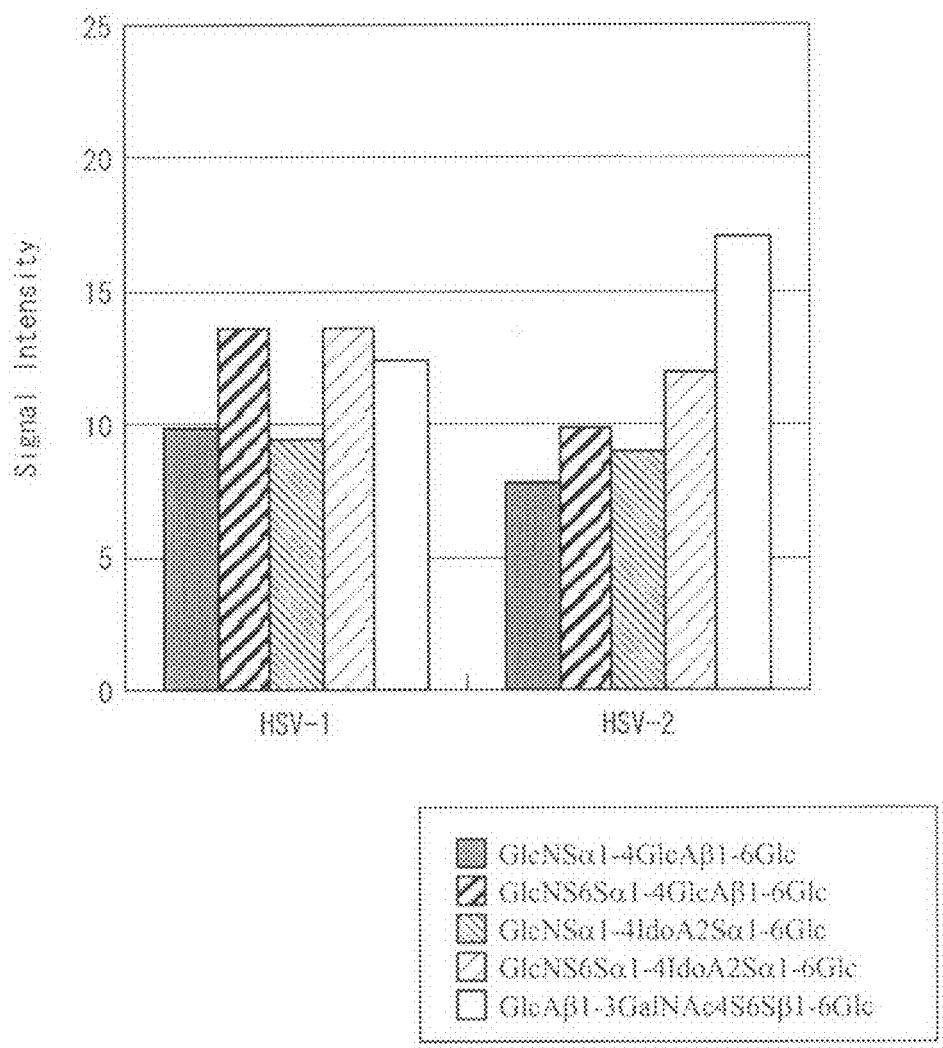
FIG. 5 is a graph illustrating results of measurement of interactions between sugar chains and herpes viruses by using a surface plasmon resonance device.
Figure 6:
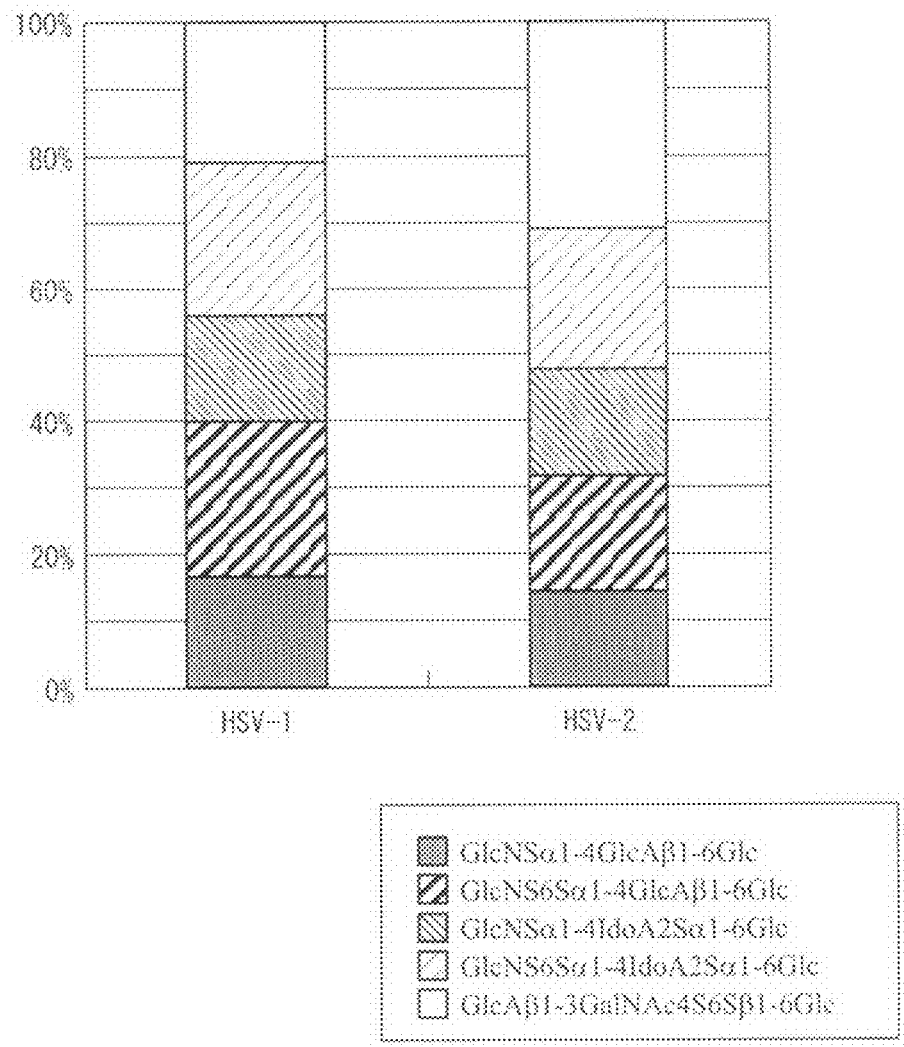
FIG. 6 is a graph illustrating ratios of reactions of 8 kinds of sugar chains to the herpes viruses where 100% is a sum of the levels (signal intensities illustrated in FIG. 5) of each reaction.

FIG. 5 is a graph illustrating results of measurement of interactions between sugar chains and herpes viruses by using a surface plasmon resonance device. FIG. 6 is a graph illustrating ratios of reactions of 8 kinds of sugar chains to the herpes viruses where 100% is a sum of the levels (signal intensities illustrated in FIG. 5) of each reaction.

FIG. 6 demonstrates that each isolated herpes virus strain exhibited different specificities to the sugar chains. That is, FIG. 6 shows that it is possible to perform patterning of the isolated herpes virus stains according to their specificities to the sugar chains.

Therefore, Example 6 demonstrates that patterning of herpes virus can be performed by measuring the interaction between isolated herpes virus stain and sugar chains.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A method of classifying influenza virus having H3N2 protein by strains, the method comprising:
    contacting a solution comprising the influenza virus having H3N2 protein with a ligand carrier,
        wherein the ligand carrier comprises a support and a plurality of ligand conjugates,
        wherein the support comprises a metal on a surface of the support, and each ligand conjugate of the plurality of ligand conjugates comprises a sugar chain bonded to a linker compound comprising a sulfur atom,
        wherein the plurality of ligand conjugates are bonded to the surface via metal-sulfur bonding due to the sulfur atom in the linker compound, and
        wherein there are 2 to 500 different kinds of the ligand conjugates, each kind of the ligand conjugate having a different sugar chain, immobilized independently on the ligand carrier per $cm^2$, such that the different kinds of the ligand conjugates are bonded to the surface in non-overlapping positions, and wherein the different kinds of ligand conjugates have differing binding specificity to different H3N2 virus strains due to the different sugar chains in the different kinds of ligand conjugates;
    measuring interactions between the influenza virus having H3N2 protein and two or more sugar chains of the plurality of ligand conjugates; and
    classifying the influenza virus having H3N2 protein by strains, based on differential binding of the influenza virus having H3N2 protein to the different kinds of ligand conjugates,
        wherein the classifying further comprises determining where the influenza virus having H3N2 protein interacts with the ligand carrier relative to the positions of the different kinds of ligand conjugates of the plurality of ligand conjugates.

2. The method as set forth in claim 1, wherein the structure of the linker compound is represented by:

$$X-\underset{\substack{\|\\O}}{C}-(CH_2)n-Y \quad (1)$$

$n = 0\text{-}6$ where X is a structure that includes one hydrocarbon chain which has a terminal aromatic amino group with a carbon-nitrogen bond in its main chain, and Y is a hydrocarbon structure having the sulfur atom, and n is not less than 0 but not more than 6.

3. The method as set forth in claim 1, wherein
the sugar chains are at least two selected from the group consisting of: Galβ1-4Glc, Galβ1-4GlcNAcβ1-6Glc, Neu5Acα2-3Galβ1-4Glc, Neu5Acα2-6Galβ1-4Glc, Neu5Acα2-3Galβ1-3GlcNAcβ1-6Glc, Neu5Acα2-6Galβ1-3GlcNAcβ1-6Glc, Neu5Acα2-3Galβ1-4GlcNAcβ1-6Glc, Neu5Acα2-6Galβ1-4GlcNAcβ1-6Glc, GlcAβ1-3GalNAc4Sβ1-6Glc, GlcAβ1-3GalNAc6Sβ1-6Glc, GlcA2Sβ1-3GalNAc6Sβ1-6Glc, GlcAβ1-3GalNAc4S6Sβ1-6Glc, GlcNS6Sα1-4IdoA2Sα1-6Glc, GlcNSα1-4IdoA2Sα1-6Glc, GlcNS6Sα1-4GlcA2Sβ1-6Glc, and GlcNSα1-4GlcAβ1-6Glc.

4. A kit for performing a method of classifying influenza virus having H3N2 protein by strains, the kit comprising:
a solution comprising the influenza virus having H3N2 protein; and
a ligand carrier, wherein the ligand carrier comprises a support and a plurality of ligand conjugates, wherein the support comprises a metal on a surface of the support, and each ligand conjugate of the plurality of ligand conjugates comprises a sugar chain bonded to a linker compound comprising a sulfur atom,
wherein the plurality of ligand conjugates are bonded to the surface via metal-sulfur bonding due to the sulfur atom in the linker compound and wherein there are 2 to 500 different kinds of the ligand conjugates, each kind of the ligand conjugate having a different sugar chain, immobilized independently on the ligand carrier per cm$^2$, such that the different kinds of ligand conjugates are bonded to the surface in non-overlapping positions, and
wherein the different kinds of ligand conjugates have differing binding specificity to the different H3N2 virus strains due to the different sugar chains in the different kinds of ligand conjugates, and
wherein the kit is configured to classify influenza virus having H3N2 protein by strain based on differential binding of the influenza virus to the different kinds of ligand conjugates, wherein the classification comprises determining where the influenza virus interacts with the ligand carrier relative to the positions of the different kinds of ligand conjugates of the plurality of ligand conjugates.

5. The kit as set forth in claim 4, wherein the sugar chains are at least two selected from the group consisting of: Galβ1-4Glc, Galβ1-4GlcNAcβ1-6Glc, Neu5Acα2-3Galβ1-4Glc, Neu5Acα2-6Galβ1-4Glc, Neu5Acα2-3Galβ1-3GlcNAcβ1-6Glc, Neu5Acα2-6Galβ1-3GlcNAcβ1-6Glc, Neu5Acα2-3Galβ1-4GlcNAcβ1-6Glc, Neu5Acα2-6Galβ1-4GlcNAcβ1-6Glc, GlcAβ1-3GalNAc4Sβ1-6Glc, GlcAβ1-3GalNAc6Sβ1-6Glc, GlcA2Sβ1-3GalNAc6Sβ1-6Glc, GlcAβ1-3GalNAc4S6Sβ1-6Glc, GlcNS6Sα1-4IdoA2Sα1-6Glc, GlcNSα1-4IdoA2Sα1-6Glc, GlcNS6Sα1-4GlcA2Sβ1-6Glc, and GlcNSα1-4GlcAβ1-6Glc.

6. The method of claim 1, wherein in the measuring the interactions between the influenza virus having H3N2 protein and the two or more sugar chains of the plurality of ligand conjugates, a strength of the interactions between the influenza virus having H3N2 protein and the two or more sugar chains of the plurality of ligand conjugates is measured.

7. The method of claim 1, wherein in the measuring the interactions between the influenza virus having H3N2 protein and the two or more sugar chains of the plurality of ligand conjugates, the interactions between the influenza virus having H3N2 protein and the two or more sugar chains of the plurality of ligand conjugates are measured concurrently.

* * * * *